United States Patent
Corbin

(10) Patent No.: US 9,889,092 B2
(45) Date of Patent: Feb. 13, 2018

(54) LOW DENSITY LIPOPROTEIN NANOCARRIERS FOR TARGETED DELIVERY OF OMEGA-3 POLYUNSATURATED FATTY ACIDS TO CANCER

(71) Applicant: The Board of Regents of the University of Texas System, Austin, TX (US)

(72) Inventor: Ian R. Corbin, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/774,637

(22) PCT Filed: Mar. 13, 2014

(86) PCT No.: PCT/US2014/025334
§ 371 (c)(1),
(2) Date: Sep. 10, 2015

(87) PCT Pub. No.: WO2014/159851
PCT Pub. Date: Oct. 2, 2014

(65) Prior Publication Data
US 2016/0015636 A1    Jan. 21, 2016

Related U.S. Application Data

(60) Provisional application No. 61/780,553, filed on Mar. 13, 2013.

(51) Int. Cl.
*A61K 9/127* (2006.01)
*A61K 9/00* (2006.01)
*A61K 9/51* (2006.01)
*A61K 45/06* (2006.01)
(Continued)

(52) U.S. Cl.
CPC .......... *A61K 9/1275* (2013.01); *A61K 9/0019* (2013.01); *A61K 9/5123* (2013.01); *A61K 31/202* (2013.01); *A61K 45/06* (2013.01); *A61N 5/10* (2013.01)

(58) Field of Classification Search
CPC ........................... A61K 31/202; A61K 9/5123
See application file for complete search history.

(56) References Cited

U.S. PATENT DOCUMENTS 7,820,184 B2    10/2010    Stritzker et al.
2005/0130937 A1    6/2005    Dror et al.
(Continued)

OTHER PUBLICATIONS

Zimet et al., "Re-assembled casein micelles and casein nanoparticles as nano-vehicles for w-3 polyunsaturated fatty acids", 2011, Food Hydrocolloids, vol. 25, pp. 1270-1276.*
(Continued)

*Primary Examiner* — Michael B. Pallay
(74) *Attorney, Agent, or Firm* — Parker Highlander PLLC

(57) ABSTRACT

An LDL nanocarrier is an effective and appropriate transporter for DHA in biological systems. The LDL-DHA nanoparticle was shown to be preferentially cytotoxic to malignant liver cells. These LDL-DHA nanoparticles show great promise as an anti-cancer agent. In particular embodiments, the nanoparticles exhibit a diameter of 15 to 30 nm.

19 Claims, 26 Drawing Sheets

(51) Int. Cl.
A61K 31/202 (2006.01)
A61N 5/10 (2006.01)

(56) References Cited

U.S. PATENT DOCUMENTS

| | | | |
|---|---|---|---|
| 2008/0112914 A1* | 5/2008 | Cho | A61K 8/11 424/70.22 |
| 2008/0253960 A1* | 10/2008 | Zheng | A61K 41/0071 514/1.1 |
| 2010/0047163 A1 | 2/2010 | Forte et al. | |

OTHER PUBLICATIONS

Aggerbeck et al., "Enzymatic probes of lipoprotein structure. Hydrolysis of human serum low density lipoprotein-2 by phospholipase A2," *J Biol Chem*, 251:3823-3830, 1976.

Conquer et al., "Effect of supplementation with different doses of DHA on the levels of circulating DHA as non-esterified fatty acid in subjects of Asian Indian background," *J Lipid Res*, 39:286-292, 1998.

Dippenaar et al., "The reversibility of cancer: evidence that malignancy in human hepatoma cells is gamma-linolenic acid deficiency-dependent," *S. Afr Med J*, 62:683-685, 1982.

Dippenaar et al., "The reversibility of cancer: evidence that malignancy in melanoma cells is gamma-linolenic acid deficiency-dependent," *S. Afr Med J*, 62:505-509, 1982.

Duh et al., "Oxidative stability of polyunsaturated fatty acids and soybean oil in an aqueous solution with emulsifiers," *J Amer Oil Chem Soc*, 76:201-204, 1999.

Edwards et al., "Differential effects of delivery of omega-3 fatty acids to human cancer cells by low-density lipoproteins versus albumin," *Clin Cancer Res*, 10:8275-8283, 2004.

Firestone, "Low-density lipoprotein as a vehicle for targeting antitumor compounds to cancer cells," *Bioconjug Chem*, 5:105-113, 1994.

Gleissman et al., "Omega-3 fatty acid supplementation delays the progression of neuroblastoma in vivo," *Int J Cancer*, 2011.

Gupta et al., "Fat embolism," *Continuing Education in Anaesthesia Critical Care & Pain*, 7:148-151, 2007.

Gura, "Reversal of parenteral nutrition-associated liver disease in two infants with short bowel syndrome using parenteral fish oil: implications for future management," *Pediatrics*, 118(1):e197-201, 2006.

Hammel et al., "Structural characterisation of nucleoside loaded low density lipoprotein as a main criterion for the applicability as drug delivery system," *Chem Phys Lipids*, 123:193-207, 2003.

Heurtault et al., "Physico-chemical stability of colloidal lipid particles," *Biomaterials*, 24:4283-4300, 2003.

Hevonoja et al., "Structure of low density lipoprotein (LDL) particles: basis for understanding molecular changes in modified LDL," *Biochim Biophys Acta*, 1488:189-210, 2000.

Jayaraman et al., "Effects of oxidation on the structure and stability of human low-density lipoprotein," *Biochemistry*, 46:5790-5797, 2007.

Kader et al., "Drug targeting using low density lipoprotein (LDL): physicochemical factors affecting drug loading into LDL particles," *J Control Release*, 55:231-243, 1998.

Kang et al., "Docosahexaenoic acid induces apoptosis in MCF-7 cells in vitro and in vivo via reactive oxygen species formation and caspase 8 activation," *PLoS One*, 5:e10296, 2010.

Kanno et al., "Albumin modulates docosahexaenoic acid-induced cytotoxicity in human hepatocellular carcinoma cell lines," *Toxicol Lett*, 200:154-161, 2011.

Khan et al., "Tocopherols and phospholipids enhance the oxidative stability of borage and evening primrose triacylglycerols," Journal of Food Lipids, 7:143-150, 2000.

Krieger et al., "Replacement of neutral lipids of low density lipoprotein with esters of long chain unsaturated fatty acids," *J Biol Chem*, 254:3845-3853, 1979.

Krieger, "Reconstitution of the hydrophobic core of low-density lipoprotein," *Methods in Enzymology*, 128:608-613, 1986.

Leary et al., "Some effects of gamma-linolenic acid on cultured human oesophageal carcinoma cells," *S Afr Med J*, 62:681-683, 1982.

Lee et al., "The cell cycle effects of docosahexaenoic acid on human metastatic hepatocellular carcinoma proliferation," *International Journal of Oncology*, 36:991-998, 2010.

Lestavel-Delattre et al., "Low-density lipoprotein for delivery of an acrylophenone antineoplastic molecule into malignant cells," *Cancer Res*, 52:3629-3635, 1992.

Lim et al., "Omega-3 polyunsaturated fatty acids inhibit hepatocellular carcinoma cell growth through blocking β-catenin and cyclooxygenase-2," *Mol Cancer Ther*, 8(11):3046-3055, 2009.

Lindskog et al., "Neuroblastoma cell death in response to docosahexaenoic acid: sensitization to chemotherapy and arsenic-induced oxidative stress," *Int J Cancer*, 118:2584-2593, 2006.

Lou et al., "High-density lipoprotein as a potential carrier for delivery of a lipophilic antitumoral drug into hepatoma cells," *World J Gastroenterol*, 11(7):954-959, 2005.

Lutz et al., "Fat emulsion particle size: influence on the clearance rate and the tissue lipolytic activity," *Am J Clin Nutr*, 50:1370-1381, 1989.

Masquelier et al., "Plasma stability and cytotoxicity of lipophilic daunorubicin derivatives incorporated into low density lipoproteins," *Eur J Med Chem*, 35:429-438, 2000.

Masquelier et al., "Low density lipoprotein as a carrier of cytostatics in cancer chemotherapy: study of stability of drug-carrier complexes in blood," *J Drug Target*, 8:155-164, 2000.

Miyashita et al., "Oxidative stability of polyunsaturated fatty acids in an aqueous solution," *Bioscience, Biotechnology, and Biochemistry*, 57:1638-1640, 1993.

Namani et al., "Vesicles from docosahexaenoic acid," *Colloids Surf B Biointerfaces*, 54:118-123, 2007.

Noguchi et al., "Chemoprevention of DMBA-induced mammary carcinogenesis in rats by low-dose EPA and DHA," *Br J Cancer*, 75:348-353, 1997.

Oliveira et al., "Triglyceride hydrolysis of soy oil vs fish oil emulsions," *J Parenter Enteral Nutr*, 21:224-229, 1997.

PCT International Preliminary Report on Patentability issued in International Application No. PCT/US2014/025334, dated Sep. 24, 2015.

PCT International Search Report and Written Opinion issued in International Application No. PCT/US2014/025334, dated Sep. 19, 2014.

Reynolds et al., "Low-density lipoprotein-mediated delivery of docosahexaenoic acid selectively kills murine liver cancer cells," *Nanomedicine* (Lond), 9(14):2123-2141, 2014.

Roche et al., "The antioxidant properties of serum albumin," *FEBS Lett*, 582:1783-1787, 2008.

Segrest et al., "Structure of apolipoprotein B-100 in low density lipoproteins," *J Lipid Res*, 42:1346-1367, 2001.

Shangguan et al., "Identification of liver cancer-specific aptamers using whole live cells," *Anal Chem*, 80:721-728, 2008.

Swamy et al., "Prevention and treatment of pancreatic cancer by curcumin in combination with omega-3 fatty acids," *Nutr Cancer*, 60(Suppl 1):81-89, 2008.

Wang et al., "Apolipoprotein B is conformationally flexible but anchored at a triolein/water interface: a possible model for lipoprotein surfaces," *Proc Natl Acad Sci U S A*, 103:6871-6876, 2006.

Zimet et al., "Beta-lactoglobulin and its nanocompelxes with pectin as vehicles for ω-3 polyunsaturated fatty acids," *Food Hydrocoll*, 23:1120-1126, 2009.

Zimet et al., "Re-assembled casein micelles and casein nanoparticles as nano-vehicles for omega-3 polyunsaturated fatty acids," *Food Hydrocolloids*, 25:1270-1276, 2011.

* cited by examiner

LDLR PROTEIN EXPRESSION

MODE OF CELL DEATH

LOW DENSITY LIPOPROTEIN NANOCARRIERS FOR TARGETED DELIVERY OF OMEGA-3 POLYUNSATURATED FATTY ACIDS TO CANCER

This application is a national phase application under 35 U.S.C. § 371 of International Application No. PCT/US2014/025334, filed Mar. 13, 2014, which claims benefit of priority to U.S. Provisional Application Ser. No. 61/780,553, filed Mar. 13, 2013, the entire contents of each of which are hereby incorporated by reference.

The invention was made with government support under Grant No. U24 CA126608 awarded by the National Institutes of Health. The government has certain rights in the invention.

BACKGROUND OF THE INVENTION

1. Field of the Invention

The present invention relates generally to the field of cancer treatment. More particularly, it concerns methods of generating DHA-containing lipid nanoparticles and their use in the treatment of cancer.

2. Description of Related Art

In recent years, the dietary benefits of omega-3 polyunsaturated fatty acids (ω-3 PUFA) have not only been heralded for improving cardiovascular health, but also for preventing cancer. Numerous population ecological studies have shown that a high per capita consumption of cold water fish (a high source of ω-3 PUFAs) correlates with lower risk of cancer (Hursting et al., 1990; Caygill et al. 1996; Sasaki et al., 1993; Sasazuki et al.; 2011; Sawada et al., 2012). The active anti-cancer components in fish oil are the PUFAs eicosapentaenoic acid (EPA) and docosahexaenoic acid (DHA). Animal studies also support this inverse association, as they have shown that high dietary intake of ω-3 PUFAs can markedly impede experimental carcinogenesis (Sasazuki et al.; 2011; Sawada et al., 2012; Berquin et al., 2007; Iwamoto et al., 1998; Braden et al., 1986; Rose et al., 1993). Collectively, these epidemiologic and preclinical studies indicate that high dietary ω-3 PUFAs can antagonize the initiation and early progression of cancer in situ.

It is less clear what role or benefit ω-3 PUFAs may have in the treatment of pre-existing tumors. To date, many papers have demonstrated the dose-dependent cytotoxicity of ω-3 PUFAs towards various cancer cells in culture (Kang et al., 2010; Lim et al., 2009; Lindskog et al., 2006). However, the local doses of ω-3 PUFAs used to elicit these anticancer effects in culture are difficult, if not impossible, to achieve through dietary consumption (Conquer and Holub, 1998). This likely explains why the few studies that attempted to treat established tumors through dietary consumption of ω-3 PUFAs reported inconsistent results with only modest effects (Gleissman et al., 2010; Noguchi et al., 1997; Swamy et al., 2008). Direct intravascular administration of ω-3 PUFAs is not a feasible option due to their poor aqueous solubility and propensity to form emboli (Gupta et al., 2007; Namani et al., 2007). Even for the cell culture experiments mentioned above, organic solvents, such as ethanol or dimethyl sulfoxide, were required to solubilize the ω-3 PUFAs in cell culture media. Alternatively albumin can be used as a physiological transporter for ω-3 PUFAs, however, there are some concerns that albumin may protect cancer cells against ω-3 PUFA-induced cytotoxicity (Kanno et al., 2011; Roche et al., 2008). Fish oil-based emulsions used for parenteral nutrition (e.g., Omegaven) can transport large amounts of ω-3 PUFAs in the plasma. However, their large heterogeneous size (diameters >200 nm), rapid clearance by the mononuclear phagocyte system (MPS) and poor sensitivity to lipoprotein lipase limit their efficacy to deliver ω-3 PUFAs to tumors (Gura, 2006; Lutz et al., 1989; Oliveira et al., 1997).

SUMMARY OF THE INVENTION

In one embodiment, the present disclosure provides a composition comprising a lipid nanoparticle comprising a ω-3 polyunsaturated fatty acid and lacking another anti-cancer agent. In another embodiment, a composition comprising a lipid nanoparticle consisting essentially of low density lipoprotein (LDL) and a ω-3 polyunsaturated fatty acid is provided. In a further embodiment, a composition comprising a lipid nanoparticle and a therapeutically effective amount of a ω-3 polyunsaturated fatty acid not conjugated to another anti-cancer agent is provided.

In one aspect of the present embodiments, a lipid nanoparticle may be a LDL or sLDL nanoparticle. The LDL may be human LDL. In one aspect, ApoB100 is embedded in a phospholipid monolayer of the LDL or sLDL nanoparticle. Said lipid nanoparticle or LDL or sLDL nanoparticle of the present disclosure may have a diameter of about 15 nm to about 30 nm.

In one aspect of the present embodiments, a ω-3 polyunsaturated fatty acid is docosahexaenoic acid (DHA) 22:6 (n-3). In additional aspects, the ω-3 polyunsaturated fatty acid may be, but is not limited to, hexadecatrienoic acid (HTA) 16:3 (n-3), α-linolenic acid (ALA) 18:3 (n-3), stearidonic acid (SDA) 18:4 (n-3), eicosatrienoic acid (ETE) 20:3 (n-3), eicosatetraenoic acid (ETA) 20:4 (n-3), eicosapentaenoic acid (EPA) 20:5 (n-3), heneicosapentaenoic acid (HPA) 21:5 (n-3), docosapentaenoic acid (DPA) (clupanodonic acid) 22:5 (n-3), tetracosapentaenoic acid 24:5 (n-3), tetracosahexaenoic acid (nisinic acid) 24:6 (n-3), γ-linolenic acid (GLA) 18:3 (n-6), arachidonic acid 20:4 (n-6), or adrenic acid 22:4 (n-6).

In one aspect, the present invention provides a composition comprising an LDL nanoparticle comprising DHA and lacking another anti-cancer agent. In other aspect, a composition comprising a nanoparticle consisting essentially of LDL and DHA is provided. In a further aspect, a composition comprising a LDL nanoparticle and a therapeutically effective amount of DHA not conjugated to another anti-cancer agent is provided. In these aspects, DHA may be incorporated into the LDL structure.

In certain aspects, the compositions of the embodiments are comprised in a pharmaceutically acceptable carrier.

In another embodiment, the present disclosure provides a method for treating a subject having a cancer comprising administering an effective amount of a composition of the embodiments to the subject. In certain aspects, the cancer may be a breast cancer, lung cancer, head and neck cancer, prostate cancer, esophageal cancer, tracheal cancer, brain cancer, liver cancer, bladder cancer, stomach cancer, pancreatic cancer, adrenal cancer, ovarian cancer, uterine cancer, cervical cancer, testicular cancer, colon cancer, rectal cancer, blood cancer, or skin cancer. The cancer may be metastatic, recurrent, or multi-drug resistant.

In one aspect, the composition is administered systemically. In additional aspects, the composition may be administered intravenously, intradermally, intratumorally, intramuscularly, intraperitoneally, or subcutaneously. In a further aspect, the composition is administered by infusion local or regional to a tumor site. Local or regional infusion may be hepatic artery infusion.

In one aspect, the method for treating further comprises administering at least a second anticancer therapy to the subject. The second anticancer therapy may be a surgical therapy, chemotherapy, radiation therapy, cryotherapy, hormonal therapy, toxin therapy, immunotherapy or cytokine therapy.

In one aspect, the subject is a human. In another aspect, the subject is a non-human mammal. In one aspect, the composition may be administered at least a second time. The composition may be administered over a period of 1 week to 6 months.

In one embodiment, the present disclosure provides a kit comprising a composition of the embodiments.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Schematic drawing of LDL-DHA nanoparticle. (FIG. 1B) Transmission electron microscopy images of native LDL (top) and LDL-DHA (bottom).

(FIG. 2A) Phospholipid content (%) relative to baseline measure; (**) $p<0.01$, LDL BL versus LDL after 1 month. (FIG. 2B) Protein content (%) relative to baseline measure; (*) $p<0.1$, LDL BL versus LDL after 1 month. (FIG. 2C) Protein secondary structure analysis using circular dichroism; () $p<0.01$, LDL BL versus LDL after 1 month β-sheet and (*) $p<0.001$, LDL BL versus LDL after 1 month α-helix.

(FIG. 3A) Z-average particle size; (FIG. 3B) polydispersity index; (*) $p<0.1$, LDL Baseline or LDL after 2 weeks versus LDL after 4 weeks. (FIG. 3C) zeta potential; () $p<0.01$, LDL Baseline or LDL after 2 weeks versus LDL after 4 weeks. (FIG. 3D) % transmittance; () $p<0.0001$, LDL Baseline versus LDL after 2 weeks or LDL after 4 weeks; (*) $p<0.001$, LDL after 2 weeks versus LDL after 4 weeks. Z-average particle size is expressed as particle diameter in nm. Zeta potential is expressed as mV.

(FIG. 4A) HPLC determination of DHA content in LDL nanoparticles and DHA in heptane; () $p<0.01$ DHA in heptane versus LDL-DHA, after 14 days; (*) $p<0.001$, DHA in heptane versus LDL-DHA, after 21 and 28 days. (FIG. 4B) Peroxide indices of LDL, DHA in heptane, and LDL-DHA nanoparticles. Samples from FIG. 4A and FIG. 4B were stored at ambient conditions and were subjected to HPLC or peroxide analysis at baseline, 7, 14, 21, and 28 days; () $p<0.01$, DHA in heptane versus LDL-DHA after 14 days; (*) $p<0.001$, LDL or DHA in heptane versus LDL-DHA after 21 and 28 days; (****) $p<0.0001$, LDL versus LDL-DHA, after 28 days. (FIG. 4C) Peroxide indices of LDL, DHA in heptane, and LDL-DHA nanoparticles over a 4 day period (baseline, 1 day and 4 days) at 40° C.; (*) $p<0.1$, DHA in heptane versus LDL-DHA, after 24 h; () $p<0.01$, LDL and DHA in heptane versus LDL-DHA, after 96 h. (FIG. 4D) Peroxide indices of LDL, DHA in heptane, and LDL-DHA nanoparticles at baseline and after a 5 hour incubation at 55° C.; (*) $p<0.001$, LDL or DHA in heptane versus LDL-DHA, after oxidation at 55° C. DHA content is expressed as a percentage of baseline control. The peroxide index is expressed as mEq of peroxide/Kg of lipid.

(FIG. 5A) Representative western blot of LDLR expression in TIB-73 and TIB-75 cells with β-actin expression as a protein loading control. (FIG. 5B-C) The binding and uptake of 10 μg/mL LDL-DiI (FIG. 5B) or LDL-DHA-DiI (FIG. 5C) in TIB-73 and TIB-75 cells following a two hour incubation at 4° C. (external binding) or 37° C. (total binding and uptake). Internalization of LDL-DiI or LDL-DHA-DiI is calculated from the difference of 37° C. and 4° C. experiments. Values are expressed as μg LDL-DiI or LDL-DHA-DiI per mg of cell protein. Values represent the mean of 4 independent experiments where each condition was performed in duplicate. (FIG. 5D) Fluorescent images of TIB-73 and TIB-75 cells treated with 10 μg/mL LDL-DiI or 10 μg/mL LDL-DiI and excess native LDL (500 μg/mL) for 2 hours at 37° C.

(FIG. 6D) Co-cultures of TIB-73 (right) and TIB-75 (left) cells were treated with 60 μM LDL-DHA or LDL-TO for 72 hours. After treatment, the cells were imaged at 10× magnification on an inverted bright field microscope and at 0.5 magnification on a dissecting scope. *Triolein dose is equivalent to three oleic fatty acid chains (e.g., 50 μM TO is ≈150 μM OA)

(FIGS. 7A-F) Fluorescence microscopy of TIB-73 and TIB-75 cells following a 72 hr treatment with LDL nanoparticles (40 μM). The mode of cell death was assessed by staining the cells with Annexin V-FITC to detect apoptosis and propidium iodide to detect necrosis. The treatment groups are as follows: (FIG. 7A) TIB-73 Untreated; (FIG. 7B) TIB-73 LDL-TO treated; (FIG. 7C) TIB-73 LDL-DHA treated; (FIG. 7D) TIB-75

Untreated; (FIG. 7E) TIB-75 LDL-TO treated; and (FIG. 7F) TIB-75 LDL-DHA treated. (FIG. 7G) Quantitative analysis of the same treatment groups was performed by FACS analysis using two-color flow cytometric measurements. Quadrant gating was used to determine percentage of cells in different stages of apoptosis and necrosis. Results are expressed as percentage of total cell population. (**) $p<0.01$, 75 Untreated or 75 LDL-TO Treated versus 75 LDL-DHA Treated.

(FIG. 8A) Fluorescence microscopy of TIB-73 (left) and TIB-75 (right) cells at baseline and 24 hours following treatment with 60 μM LDL-TO or LDL-DHA. All cells were stained with 15 μM carboxy-H2DCFDA for 1 hour at 37° C. and imaged with an inverted fluorescent microscope (20× mag.). (FIG. 8B) Quantification of DCF fluorescence in TIB-73 and TIB-75 cells by fluorometer (ex. 485 nm and em. 526 nm). Values represent the fold difference in DCF fluorescence per mg of cell protein normalized to the untreated cells. Each value is the mean of three independent experiments. (*) $p<0.001$ (FIG. 8C) TBARS analysis of TIB-73 and TIB-75 cells at baseline and 24 hours following treatment with 40 μM LDL-TO or LDL-DHA. TBARS values were normalized to cell protein. Each value is the mean of five independent measurements. () $p<0.0001$ (FIG. 8D) Cell viability assay of TIB-75 cells following 72 hours of treatment with 40 μM LDL-DHA with or without 100 or 200 μM Vitamin E Each value represents the mean of four independent experiments. () $p<0.01$.

DESCRIPTION OF ILLUSTRATIVE EMBODIMENTS

Figure 1A:
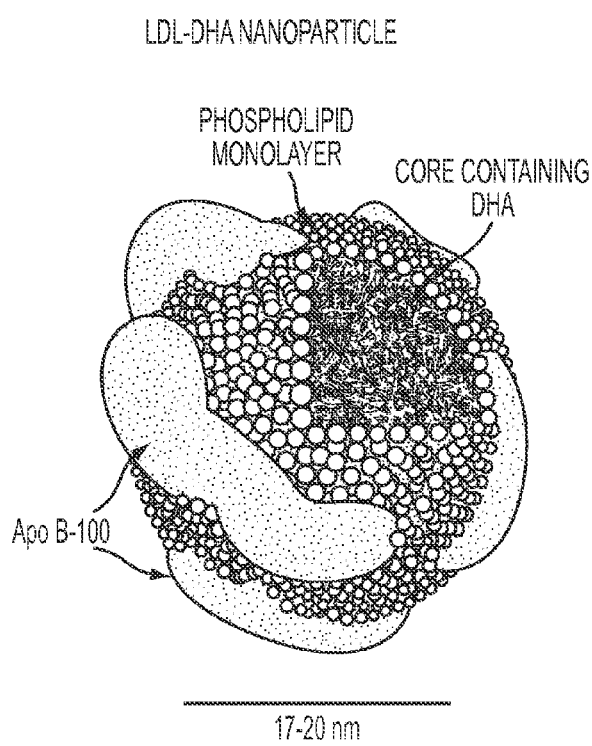
FIGS. 1A-B. LDL-DHA Nanoparticle.

Over the last decade, there have been a plethora of studies reporting on the utility of lipoprotein based nanoparticles to deliver diagnostic and/or therapeutic agents to cancer (Hill et al., 2010; Marotta et al., 2011; Murakami et al., 2010; Shazad et al., 2011; Skajaa et al., 2011; Zhou et al., 2010; Corbin et al., 2010). These carriers are attractive vehicles for oncology applications due to their nanoscale size, fine particle size distribution, high payload carrying capacity and ability to avoid MPS surveillance (Gotto et al., 1986). Furthermore cancer cells have a natural proclivity to actively take up lipoproteins to acquire lipids needed for their rapid membrane turnover (Favre, 1992; Gal et al., 1981; Ho et al., 1978). The lipoprotein platform is also a particularly fitting vehicle for $\omega$-3 PUFAs, as these carriers naturally function to transport lipids in the plasma (Gotto et al., 1986).

The natural long chain omega-3 polyunsaturated fatty acid docosahexaenoic acid (DHA) has long been credited for its benefits on cardiovascular health. In recent years DHA has also been recognized for its anticancer actions to inhibit the growth and promote the death of cancer cells. Current methods of delivering DHA to malignant cells, however, are problematic due to the poor aqueous solubility of this molecule. The low-density lipoprotein (LDL) nanocarrier described in this disclosure enables the unique opportunity to treat cancers with DHA. The engineered LDL-DHA nanoparticle retains nearly all the properties of natural LDL, thus it is a fully biocompatible, biodegradable and non-immunogenic nanostructure that is able to avoid the body's defense system (reticuloendothelial system). The LDL nanocarrier allows DHA to be directly administered into the vascular system where it is protected by the LDL shell from any metabolic or degradative processes prior to arriving at its destination. ApoB-100 on the surface of the LDL nanoparticle enables it to recognize the LDL receptor (LDLR) on cells. This is particularly important as many cancer cells overexpress the LDLR. Thus through LDLR mediated endocytosis LDL-DHA can efficiently enter into the cancer cell, where DHA is subsequently liberated to unleash its cytotoxic effects.

Herein, the utility of the low-density lipoprotein as a nanoscale delivery vehicle for DHA was evaluated. In the present disclosure, DHA was uniformly incorporated into low-density lipoprotein (LDL) nanoparticles (LDL-DHA). The engineered LDL nanoparticle, uniformly loaded with DHA, was shown to possess unique physicochemical properties that enhanced the physical and oxidative stabilities of this nanoparticle over native LDL and free DHA in heptane.

With regards to its biological activity, LDL-DHA nanoparticles were avidly taken up by normal and malignant murine liver cell lines, TIB-73 and TIB-75, respectively. In TIB-73, LDL-DHA displayed similar binding kinetics as native LDL, but in TIB-75, the LDL-DHA lacked specificity and saturability for the LDL receptor. Dose response studies in these cell lines showed that LDL-DHA is selectively cytotoxic to the malignant TIB-75 cells over the normal TIB-73. Therapeutic doses of LDL-DHA that completely killed the TIB-75 were innocuous to TIB-73 leaving them unharmed. The selective induction of lipid peroxidation and reactive oxygen species was shown to play a central role in LDL-DHA mediated cancer cell death. In summary, these finding indicate that LDL-DHA shows great promise as a selective, efficacious anticancer nanotherapy agent against hepatocellular carcinoma.

Formulating DHA with LDL also imparts unexpected and non-obvious physicochemical properties to the LDL-DHA nanoparticle. The engineered LDL-DHA possesses enhanced physical and oxidative stability over its native LDL and free DHA counterparts. This is a significant advance as the use of plasma LDL and DHA often limit research and manufacturing processes due to their poor stability. Isolated native LDL can only be stored for finite periods before aggregation and degradative processes compromise the integrity of the LDL sample. Similarly, highly unsaturated fatty acids, like DHA, are sensitive to oxidative degradation resulting in off-flavors and odors negating its health benefits. By combining the LDL and DHA components together, not only is the shelf life of this complex significantly enhanced, but more importantly the integrity and biological activities of these components are preserved in this nanoparticle formulation for an unexpected but much needed application in cancer treatment.

I. Lipoprotein Nanocarriers

Lipoproteins are naturally occurring core-shell nanostructures that serve as the main transport vehicles for cholesterol and triglycerides in mammalian systems. The low-density lipoprotein (LDL) species, in particular, has drawn the attention of many cancer researchers due to the fact that many tumors over-express the LDL receptor (LDLR). Cancer cells are believed to express elevated levels of LDLR in order to compete with the host for the necessary cholesterol and fatty acids needed for active membrane turnover. In addition, LDL exhibit a fine particle size distribution (19-25 nm), have a high-payload carrying capacity (>1600 cholesterol esters and triglyceride molecules), circulate below MPS surveillance, and have a long serum half-life (2-4 days). For these reasons many investigators have attempted to use LDL as a vehicle to deliver exogenous therapeutic agents to cancer cells. To date, progress with this approach has been impeded primarily by the inability to produce highly concentrated stable drug-LDL complexes. Many of the anticancer drugs used in these studies have been bulky heterocyclic compounds that have limited incorporation into the LDL platform (10-200 molecules per LDL) and readily 'leak' from the LDL in plasma. For these reasons the majority of the published reports have been limited to cell culture experiments and a few pre-clinical rodent studies. Unlike the previous listed anticancer agents, fatty acids and triglycerides are the natural cargo for LDL. Several advantages are gained by delivering $\omega$-3 PUFAs with the LDL based nanoplatform compared to the conventional emulsions. First, LDL are much smaller (~22 nm in diameter), therefore they are able to freely transit the vascular and interestial compartments to access the tumor cell bed, unlike the larger emulsions which get trapped surrounding tumor microenvironment. Independent studies have shown that nanostructures smaller than 40 nm achieve the greatest tumor penetration as they are able to navigate through the tight interfibrillar spacing of the tumor interstitum. Once at the tumor cell bed, LDL can enter the cancer cells through the LDLR. Moreover, the kinetics of LDLR system (15,000-70,000 LDLR per cell, recycle time=10 min and life time=24 hr) is such that a given receptor can internalize scores of LDL particles (and their cargo of $\omega$-3 PUFAs) to produce a pronounced amplification affect resulting in markedly enhanced therapeutic efficacy. In one embodiment, the mean LDL nanoparticle size is 20 nm, but can be 10-30 nm. In some embodiments, the LDL nanoparticle is between 10-20 nm in size.

II. LDL-DHA Particles

Over the years, many groups have attempted to formulate various chemotherapeutics (e.g., doxorubicin, vincristine, paclitaxel, etc.) with LDL (Firestone, 1994; Kader et al., 1998; Masquelier et al., 2000a,b). However, these LDL-drug complexes suffered from poor stability, altered apoB-100 integrity and low drug loading capacity (Kader et al., 1998; Masquelier et al. 2000; Lestavel-Delattre et al., 1992; Hammel et al., 2003). In the studies herein, an alternate approach was taken towards LDL-mediated cancer therapy; instead of trying to incorporate and transport conventional chemotherapeutics in LDL, the natural lipid, DHA, was selected as the bioactive cargo. Being a natural lipid, DHA readily incorporates into LDL through the reconstitution process; over 1400 DHA molecules are accommodated into the core shell structure of LDL. This is exceptionally good loading considering that LDL's typically carry 1500 cholestryl esters. Previous investigators have tried to "enrich" plasma LDL with PUFA by feeding African Green Monkeys a diet high in ω-3 fatty acids for 3 to 5 years (Edwards et al., 2004). Subsequent purification of their plasma yielded LDL containing up to 6% DHA fatty acids. The considerable time and cost associated with this procedure combined with the relatively small increases of DHA enrichment severely limits the practicality of this dietary supplementation approach. The LDL reconstitution method (Krieger et al., 1979) offers an efficient and facile approach to incorporating DHA into LDL particles.

The LDL-DHA particles of the present invention formed from this procedure retain nearly all the physicochemical properties and biological activities as their native counterparts. Particle size, morphology and apoB-100 protein conformation were all comparable to that seen in native LDL. The only LDL-DHA parameters that did differ significantly from native LDL were the particle's concentration of phospholipids and surface charge properties (zeta potential). The LDL-DHA particles of the present invention may be formed from synthetic (sLDL) nanoparticles as described in U.S. Pat. No. 8,252,338, incorporated herein by reference in its entirety.

The amphipathic phospholipid/protein outer layer of native LDL serves to thermodynamically stabilize the hydrophobic core of the particle. Approximately 700 phospholipid molecules make up this monolayer shell which is highly dynamic and fluid, in spite of the presence of free cholesterol in the slightly deeper interfacial layer (Hevonoja et al., 2000). Similarly, the globular domains of apoB-100 flexibly surround the LDL particle in a "belt-like" manner interspersing the phospholipid layer and changing its configuration as needed (Wang et al., 2006; Segrest et al., 2001). The outer shell of LDL-DHA, as well as that of LDL-OA, contained significantly fewer numbers of phospholipids than that of native LDL. In spite of this deficit, the dynamic and flexible phospholipid/protein shell of these reconstituted nanoparticles was able to maintain the stability of their core and the entire lipoprotein structure. In fact, the overall stability of the LDL-DHA nanoparticles was observed to be superior to that of native LDL.

LDL-DHA and LDL-OA nanoparticles also had significantly greater negative surface charge compared to LDL-TO and native LDL particles. These findings were determined by zeta potential measurements and confirmed by agarose gel electrophoresis. Typically such negatively charged surface properties are associated with oxidative degradation of LDL. However, the intact apoB-100 conformation, low peroxide values and avid/intact LDLR binding affinity of these nanoparticles argue against this view. Given that only LDL particles reconstituted with free fatty acids demonstrated this property, perhaps the anionic species of the unesterified fatty acids, potentially situated in the interfacial layer, may be contributing to this negative surface charge (Aggerbeck et al., 1976; Jayaraman et al., 2007).

A. Enhanced Nanoparticle Stability

The pronounced electronegative surface charge of LDL-DHA likely contributes to the enhanced colloidal stability of this particle over its native counterpart (Jayarman et al., 2007). In general, higher zeta-potential values, regardless of their positivity or negativity, induce stronger electrostatic repulsions that resist flocculation and promote higher stability of particles (Heurtault et al., 2003). The results from the present studies were also consistent with this principle. Over the one month study period under ambient temperature and air, LDL-DHA particles maintained zeta potential values between −22 and −17 mV. Corresponding values for z-average particle size, polydispersity, and % transmittance of the LDL-DHA remained unchanged indicating good colloidal stability. Conversely, native LDL, which had a much weaker initial surface charge (−8 mV), underwent significant aggregation, as seen by the increase z-average particle size and polydispersity and the sharp drop in its % transmittance readings. At the end of the four week period, the zeta-potential value for native LDL dropped to −21 mV; these changes were the result of oxidative degradation. The corresponding levels of apoB-100 protein, secondary structure conformation and peroxide values for native LDL confirm these oxidative changes.

Figure 4A:
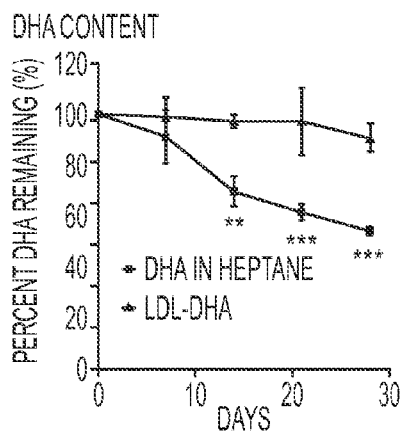
FIGS. 4A-D. Oxidative stability.

Interestingly, LDL-DHA particles were also resistant to oxidative degradation. Reconstituted DHA displayed remarkable retention and stability in the LDL particle as there was less than a 10% loss over a four week period at room temperature. Conversely, free DHA in organic solvents rapidly degrades under these conditions (FIG. 4A). The DHA molecules likely assume a tightly packed conformation in the confines of the LDL particle, similar to that of DHA micelles or emulsions in aqueous solutions. Several reports have shown that in this conformation DHA is more resistant to oxidative attack (Duh et al., 1999; Miyashita et al., 1993). In addition, the phospholipid protein shell of LDL shields the DHA from its surrounding aqueous environment and limits the accessibility of oxidizing agents to its core (Khan and Shahidi, 2000; Zimet and Liveny, 2009). Indeed, the phospholipid protein shell presents a barrier to solublized $O_2$ as its diffusion is 10 times faster in aqueous media than in the lipid milieu of LDL (Moller et al., 2005). Although $O_2$ tends to partition into lipids over water, the ordered phospholipid protein shell along with the tightly packed DHA core of the LDL particle likely constraints the dissolution of $O_2$ into the particle (Moller et al., 2005). Surprisingly, it can also be said that the incorporation of DHA into the LDL platform imparted enhanced oxidative stability to the overall LDL nanoparticle structure as well. The mechanism of this protection is unknown, but other studies corroborate these findings in demonstrating decreased oxidative susceptibility among LDLs with high DHA content (Ruiz et al., 2002; Calzada et al., 2010).

The stability of LDL-DHA was maintained even when confronted with enhanced oxidative stress. Stress test conditions involving moderate temperature elevations for prolonged periods (4 days at 40° C.) or pronounced temperature elevations for shorter durations (55° C. for 5 hrs) both induced significant peroxide production in free DHA and native LDL, indicating marked autooxidation. These findings were expected as elevated temperatures significantly increase the permeability of $O_2$, the kinetics of lipid autooxidation, and the overall denaturation of LDL (Schuster et al., 1995). However, under these same conditions the integrity of LDL-DHA nanoparticles was retained. It stands to reason that the protective mechanism described above also shielded the LDL-DHA from extensive oxidative deterioration during the stress tests.

Formulating DHA with LDL imparts unexpected and non-obvious physicochemical properties to the LDL-DHA nanoparticle. The engineered LDL-DHA possesses enhanced physical (FIGS. 2A-C and 3A-D) and oxidative (FIGS. 4A-D) stability over its native LDL and free DHA counterparts. This is a significant advance as the use of plasma LDL and DHA often limit research and manufacturing processes due to their poor stability. Isolated native LDL can only be stored for finite periods before aggregation and degradative processes compromise the integrity of the LDL sample. Similarly, highly unsaturated fatty acids, like DHA, are sensitive to oxidative degradation resulting in off-flavors and odors negating its health benefits. By combining the LDL and DHA components together, not only was the shelf life of this complex significantly enhanced, but more importantly the integrity and biological activities of these components were preserved in this nanoparticle formulation for an unexpected but much needed application in cancer treatment.

B. Biological Activity of LDL-DHA

The biological activity of the LDL-DHA nanoparticles was evaluated in the paired normal and malignant murine liver cell lines, TIB-73 and TIB-75, respectively. TIB-73 is an immortalized hepatocyte cell line derived from the liver of BALB/c mice that is not tumorigenic when injected into mice (Shangguan et al., 2008). TIB-75 is a HCC cell line derived from TIB-73 by transformation with methylcholanthrene epoxide (Patek et al., 1978). TIB-75 is tumorigenic when injected into mice (Shangguan et al., 2008). Comparative studies of these two cell lines offer an excellent opportunity for identifying cancer specific pathways and sensitivities. Distinct differences were noted in their morphology in cell culture. The TIB-73 displayed typical cobblestone epithelial growth patterns. Conversely, TIB-75 demonstrated more chaotic mesenchymal morphology consistent with a malignant phenotype (Ogunwobi and Liu, 2011). The differences in the expression of LDLR between the two cell lines were equally striking. Abundant protein levels of LDLR were observed in the TIB-73, which is typical for normal hepatocytes. In most accounts, malignant transformation is commonly associated with the over-expression of the LDLR protein (Nakagawa et al., 1995; Peterson et al., 1985). However, the TIB-75 displayed less LDLR than its normal counterpart. This deficit, however, did not hinder the ability of the TIB-75 cells to bind or internalize LDL (FIGS. 5A-D). Additional specific binding assays performed at 4° C. revealed that while TIB-73 cells bound LDL in an LDLR dependent manner (KD=16.67±9.2 μg protein/ml LDL-DiI; Bmax=1.66±0.23 μg LDL/mg cell protein), the TIB-75 cells bound LDL with nonsaturable kinetics. Various cell surface receptors and transporters (e.g., lipoprotein-binding site, LDLR-related protein 6, etc.) (Brissette and Falstrault, 1992; Ye et al., 2012) are likely recruited to engage and internalize LDL to compensate for the low level of LDLR.

The TIB-73 cells bound and internalized LDL-DHA in a similar LDLR dependent manner as native LDL. These results further confirm that the apoB-100 conformation and LDLR binding properties were retained in the reconstituted LDL-DHA nanoparticle. The TIB-75 cells bound LDL-DHA through non-specific and non-saturable interactions. For TIB-75 the total uptake and internalization of LDL-DHA was less than that of native LDL, indicating reduced exposure to DHA.

C. Anti-Cancer Activity

The findings of the studies herein clearly demonstrate that LDL-DHA nanoparticles preferentially kill cancer cells. Therapeutic concentrations of LDL-DHA that are lethal to monocultures of malignant TIB-75, prove to be innocuous to TIB-73. Furthermore, the co-culture experiments vividly show the ability of LDL-DHA to preferentially ablate cancer cells in the presence of normal cells. The normal TIB-73 counterparts do not experience any collateral injury during these experiments and continue to grow. Similarly, in the body malignant cells grow next to normal tissues, thus the findings of these experiments suggest that LDL-DHA may be a highly efficacious anticancer agent in vivo. Such pronounced therapeutic selectivity is rarely seen and is highly desired in oncology research. The anticancer actions of PUFAs have been reported since the early 1980's (Dippenaar et al., 1982a,b; Leary et al., 1982). In these studies, Dippenaar and colleagues proposed that the viability of cancer cells was dependent upon PUFA deficiency, they went on to show that supplementation with PUFA (particularly gamma-linolenic acid) significantly inhibited the growth of a variety of malignant cells. Since these studies, researchers have relied on organic solvents to solubilize these lipids for biological investigation. Until the studies herein, adequate physiological delivery of PUFA, apart from oral intake, remained elusive. While albumin serves as a major colloidal carrier in plasma, its limited fatty acid carrying capacity, indiscriminant distribution and ambiguous intracellular delivery potentially detract from its utility as an anticancer drug delivery vehicle. Our studies show that when DHA is associated with HSA, it is ineffective at killing TIB-75 up to doses of 200 μM. These results are corroborated by the finding of others who report that albumin mediated delivery of wω-3 PUFA only weakly inhibits proliferation or the induction of apoptosis in cancer cells (Edwards et al., 2004). Further studies by Kanno et al. concluded that albumin is able to modulate the actions of DHA and thereby protect cancer cells from DHA mediated injury (Kanno et al., 2011). The LDL nanoparticle, on the other hand, has proven to be very effective at delivering and mediating the cytotoxic actions of DHA towards cancer cells. Following internalization of the LDL-DHA complex, the liver cancer cells experience pronounced cytotoxic reactions that activate both apoptotic and necrotic processes. This mixed pattern of cell death indicates that several ante-mortem pathways are likely triggered by LDL-DHA treatment. In this event, an intense activation of death processes along multiple fronts overwhelms the homeostatic systems in the TIB-75, resulting in rapid and severe cell kill. It should be noted that the anticancer efficacy of the LDL-DHA is not dependent upon the overexpression of LDLR on cancer cells, as is seen with other receptor mediated nanotherapies. The fact that TIB-75 expresses less LDLR and takes up equal or slightly less LDL-DHA than TIB-73, suggests that the selective cytotoxicity of this therapy is mainly governed by DHA.

Therapeutic selectivity is a critical issue in cancer treatment. An ideal anticancer agent should be toxic to malignant cells with minimal toxicity in normal cells. Currently there are a limited number of such agents available for clinical use. The results from the studies herein indicate the LDL-DHA is such an agent. Therapeutic doses of LDL-DHA that completely kill liver cancer cells are innocuous to normal cells and leave them unharmed (FIGS. 6A-D). This type of selectivity is rarely seen and greatly desired for an anticancer drug.

Another non-obvious discovery of the LDL-DHA system is the fact that the anticancer activity of DHA is significantly mediated through the LDL carrier. When human serum albumin is used to transport DHA and treat cancer cells, poor anticancer activity is observed (FIG. 6C). Other independent investigators have also reported minimal anticancer effects with albumin associated DHA. This is a very important observation as dietary ingested DHA is transported to cancer cells by serum albumin. Thus therapeutic strategies of treating cancer with dietary DHA would yield highly variable results with limited success (this is in fact what is typically reported by epidemiological studies for the use of oral DHA for cancer).

To date, several mechanisms have been proposed to explain the anticancer actions of DHA, one of which is the general cytotoxic effects of fatty acids. The dual polar-nonpolar nature of non-esterified fatty acids allows these molecules to behave like detergents (Pande, 1968; Shaw, 1985). Ionized fatty acid micelles are able to solubilize membrane lipids and proteins and disrupt the integrity of cell membranes (Pande, 1968). This indiscriminant toxicity was not evident with equimolar treatments of LDL26 OA or LDL-TO, thus it can be reasoned that the cytotoxic properties of DHA cannot be explained by this general "detergent" or lipotoxic effect.

Lipid peroxidation and oxidative stress are commonly cited as pathways of DHA induced cytotoxicity due to the high oxidative susceptibility from the many bisallylic hydrogens present in this fatty acid molecule. The findings of the studies herein also support this premise. In addition to succumbing to a catastrophic cell kill, LDL-DHA treated TIB-75 cells experienced a drastic increase in the intracellular levels of lipid peroxides and ROS. During the lipid peroxidation process, the long unsaturated hydrocarbon chain of DHA is first degraded to various lipid hydroperoxides and finally to a variety of alkoxyl and peroxyl radicals (Siddiqui and Harvey, 2008). High levels of alkoxyl aldehyde end-products (e.g., malondialdehyde), as determined from their chromogen adducts with TBA, attest to escalated activities of the lipid peroxidation pathways (Ohkawa et al., 1979). Similarly, the pronounced DCF fluorescence detected in TIB-75 indicate that the ROS production in these cells far exceed their endogenous antioxidative defenses (Chen et al., 2010). The products of both pathways, the highly reactive aldehydes and ROS species, are each known to activate both apoptosis and necrosis processes (Lopez-Sanchez et al., 2007; Gardner et al., 1997; Chandra et al., 2000; Vanlangenakker et al., 2008; de Villiers et al., 2007; Chen et al., 1995). The lipid peroxidation and ROS mediated cell death of TIB-75 was later validated with studies including antioxidant supplementation. Co-incubation with vitamin E, a known suppressor of lipid peroxidation and ROS production, was able to effectively protect the TIB-75 from LDL-DHA induced cell death. The exact molecular mechanisms whereby LDL-DHA lipid peroxidation and ROS processes lead to cell death remains to be elucidated.

Concomitant analysis of the TIB-73 cells following LDL-DHA treatment revealed that they neither experienced cell kill nor elevated lipid peroxidation or ROS production. The TIB-73 cells were able to fully tolerate the LDL-DHA treatments at doses that were lethal to their malignant counterparts. It should be noted that the lack of toxicity experienced by the TIB-73 was not the result of avoidance or reduced intracellular uptake, in fact the TIB-73 internalized equal amounts or slightly more LDL-DHA (non-significant) than the TIB-75 (FIGS. 5A-D). These findings suggest that the TIB-73 were able to metabolize and process the LDL-DHA in a benign non-toxic manner.

Figure 16:
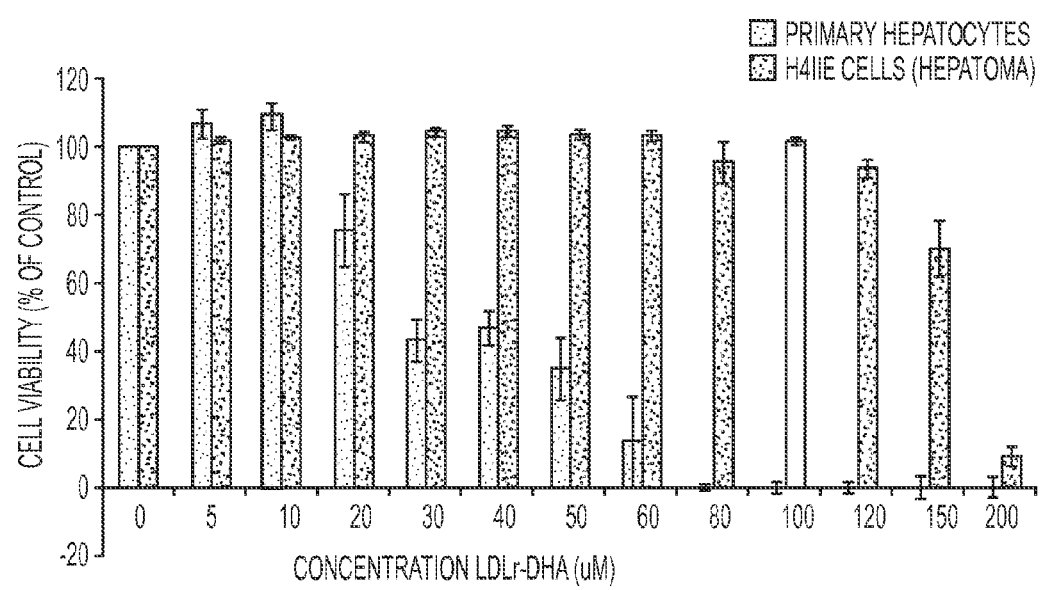
FIG. 16. Dose response of LDL-HDA in primary rat hepatocytes and rat hepatoma cells. Cell viability (MTT assay) was performed following a 72 h incubation with LDL particles. Data are mean±standard error. Left columns are primary hepatocytes. Right columns are H4IIE cells.
Figure 18:
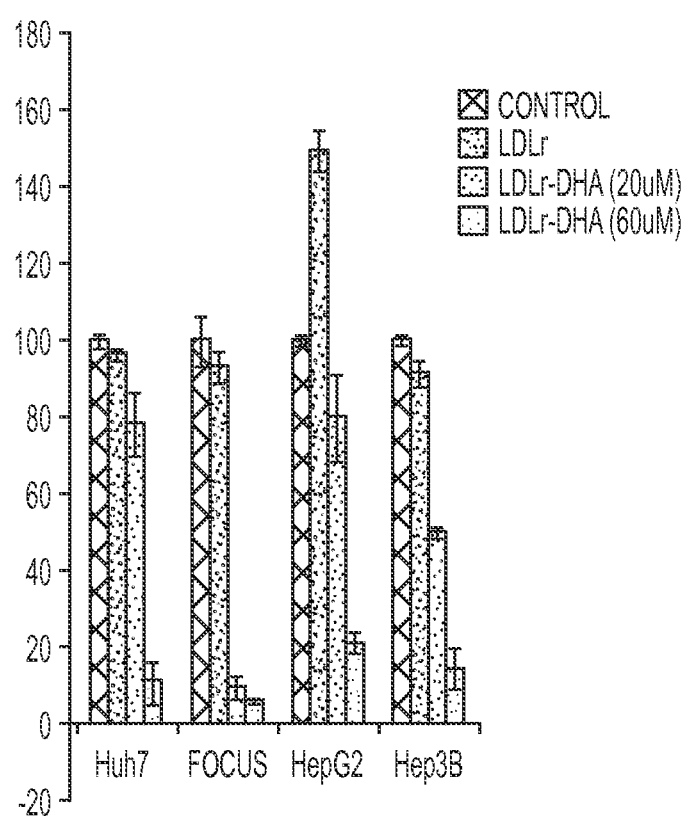
FIG. 18. Effects of LDL-DHA on malignant human hepatocellular carcinoma cells. Cell viability (MTT assay) was performed following a 72 h incubation with LDL particles. Data are mean±standard error. Left columns are Huh7; second to left columns are Focus; second to right columns are HepG2; right columns are Hep3B.

The presently disclosed LDL nanocarrier is an effective and appropriate transporter for DHA in biological systems. Incorporation of DHA into the LDL particle imparts unexpected physicochemical properties that enhanced physical and oxidative stabilities of this complex over native LDL and free DHA. Finally, the LDL-DHA nanoparticle was shown to be preferentially cytotoxic to malignant murine liver cells. Normal murine liver cells did not experience any harm from the LDL-DHA treatment at doses that were lethal to HCC cells. The therapeutic efficacy of LDL-DHA is not limited to mouse cells; both rat and human cells experience similar effects (FIGS. 16 and 18). LDL-DHA nanoparticles show great promise as an anti-cancer agent against such a challenging malignancy as HCC, further preclinical and clinical testing is warranted.

III. Treatment of Diseases

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an LDL-DHA nanoparticle to a cancer patient in need thereof.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

A. Pharmaceutical Preparations

Where clinical application of a therapeutic composition containing an inhibitory antibody is undertaken, it will generally be beneficial to prepare a pharmaceutical or therapeutic composition appropriate for the intended application. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

The therapeutic compositions of the present embodiments are advantageously administered in the form of injectable compositions either as liquid solutions or suspensions; solid forms suitable for solution in, or suspension in, liquid prior to injection may also be prepared. These preparations also may be emulsified.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 μg/kg/body weight to about 1000 mg/kg/body weight (this such range includes intervening doses) or more per administration, and any range derivable therein. In non-limiting examples of a derivable range from the numbers listed herein, a range of about 5 μg/kg/body weight to about 100 mg/kg/body weight, about 5 μg/kg/body weight to about 500 mg/kg/body weight, etc., can be administered. The practitioner responsible for administration will, in any event, determine the concentration of active ingredient(s) in a composition and appropriate dose(s) for the individual subject.

The active compounds can be formulated for parenteral administration, e.g., formulated for injection via the intravenous, intramuscular, sub-cutaneous, or even intraperitoneal routes. One preferred method of administration is hepatic artery infusion. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

B. Combination Treatments

In certain embodiments, the compositions and methods of the present embodiments involve a LDL-DHA nanoparticle, in combination with a second or additional therapy.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both a LDL-DHA nanoparticle and a second therapy. A tissue, tumor, or cell can be contacted with one or more compositions or pharmacological formulation(s) comprising one or more of the agents (i.e., LDL-DHA nanoparticle or an anti-cancer agent), or by contacting the tissue, tumor, and/or cell with two or more distinct compositions or formulations, wherein one composition provides 1) a LDL-DHA nanoparticle, 2) an anti-cancer agent, or 3) both a LDL-DHA nanoparticle and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

A LDL-DHA nanoparticle may be administered before, during, after, or in various combinations relative to an anti-cancer treatment. The administrations may be in intervals ranging from concurrently to minutes to days to weeks. In embodiments where the LDL-DHA nanoparticle is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the LDL-DHA nanoparticle therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a LDL-DHA nanoparticle therapy is "A" and an anti-cancer therapy is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

i. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelisin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine,plicomycin, gemcitabien, navelbine, farnesyl-protein tansferase inhibitors, transplatinum, and pharmaceutically acceptable salts, acids, or derivatives of any of the above.

ii. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

iii. Immunotherapy

The skilled artisan will understand that immunotherapies may be used in combination or in conjunction with methods of the embodiments. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

iv. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

v. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. Definitions

The term "consisting essentially of" when applied to the lipid nanoparticles of the present invention is defined as containing the recited elements but no other therapeutically moieties, but does not exclude the inclusion of other non-therapeutic agents.

The term "LDL" or "low density lipoprotein" refers to a class of naturally occurring lipoprotein particles, varying in their size (18-25 nm in diameter) and contents, which carry cholesterol in the blood and around the body, for use by cells. The LDL contains the apolipoproteins B-100 (Apo B-100, a protein with 4536 amino acid residues). It also contains antioxidative vitamins (vitamin E or carotinoids). It is commonly referred to as "bad cholesterol" due to the link between high LDL levels and cardiovascular disease.

The term "LDL receptor" or "LDLR" refers to a receptor that is expressed and presented on the surface of cells, and is responsible for binding LDL particles. The LDLR ligand is the Apo B-100 glycoprotein on the surface of the LDL particle.

The term "lipid moiety" refers to the lipid portion of the LDL nanoparticle. The lipid portion can be made according to methods described herein, or any suitable method of forming a liposome-type particle as known to those of skill in the art.

The term "synthetic LDL nanoparticles" or "sLDL nanoparticle" refers to a low density lipoprotein particle comprising a lipid portion and synthetic chimeric peptides. The lipid portion and the chimeric peptides can be admixed, covalently linked, or non-covalently linked. The synthetic chimeric peptides of the sLDL nanoparticle comprise an amphipathic α-helix and a lipid receptor binding domain. The amphipathic α-helices confer lipid affinity to the synthetic peptides, while LDL receptor binding domain confers affinity for LDL receptors found on the surface of cells. The lipid portion of the sLDL nanoparticle is a lipid microemulsion consisting of 3:2:1 molar ratio of phospholipids (PL), triglyceride (TG) and cholesteryl ester (CE) or any other molar ratio of lipid components that allows for microemulsification and ultimately produces a particle of 10-30 nm in size. Alternatively, the lipid microemulsion can consist of PL and TG. In some embodiments, the PL and TG are in a molar ratio of 3:2. In other embodiments, the lipid microemulsion can consist of any lipids known in the art.

It is well known to those of skill in the art that small lipid particles or liposomes can be generated by a variety of methods as described in, e.g., Szoka et al., Ann. Rev. Biophys. Bioeng. 9:467 (1980); U.S. Pat. Nos. 4,186,183, 4,217,344, 4,235,871, 4,261,975, 4,485,054, 4,501,728, 4,774,085, 4,837,028, 4,946,787; PCT Publication No. WO 91/17424; Szoka & Papahadjopoulos, Proc. Natl. Acad. Sci. USA 75: 4194-4198 (1978); Deamer & Bangham, Biochim. Biophys. Acta 443: 629-634 (1976); Fraley et al., Proc. Natl. Acad. Sci. USA 76: 3348-3352 (1979); Hope et al., Biochim. Biophys. Acta 812: 55-65 (1985); Malyer et al., Biochim. Biophys. Acta 858: 161-168 (1986); Williams et al., Proc. Natl. Acad. Sci. USA 85: 242-246 (1988), Liposomes, ch. 1 (Ostro, ed., 1983); and Hope et al., Chem. Phys. Lip. 40: 89 (1986). Suitable methods include, e.g., sonication, extrusion, high/pressure/homogenization, microfluidization, detergent dialysis, calcium-induced fusion of small liposome vesicles, and ether-infusion methods, all well known in the art. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be re-dissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate. For instance, suspending the lipids of choice in solution and sonicating the solution can be used to generate lipid microemulsions containing lipid particles. The resulting particles of choice can then be separated using various density gradients or using size exclusion chromatography. Other methods are well known to those of skill in the art.

Following liposome preparation, the liposomes that have not been sized during formation may be sized by extrusion to achieve a desired size range and relatively narrow distribution of liposome sizes. A size range of about 0.2-0.4 microns allows the liposome suspension to be sterilized by filtration through a conventional filter, typically a 0.22 micron filter. The filter sterilization method can be carried out on a high through-put basis if the liposomes have been sized down. Several techniques are available for sizing liposomes to a desired size. One sizing method is described in U.S. Pat. No. 4,529,561 or 4,737,323. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. The size of the liposomal vesicles may be determined by quasi-electric light scattering (QELS) as described in Bloomfield, Ann. Rev. Biophys. Bioeng., 10: 421-450 (1981). Average liposome diameter may be reduced by sonication of formed liposomes. Intermittent sonication cycles may be alternated with QELS assessment to guide efficient liposome synthesis.

The term "apolipoprotein" or "Apo" refers to any one of several helical proteins that can combine with a lipid (i.e., solubilize the lipid) to form a lipoprotein and are a constituent of chylomicrons, HDL, and VLDL. Apolipoproteins exert their physiological effect on lipid metabolism by binding to and activating specific enzymes or transporting proteins or lipids to cells via specific receptors, e.g., LDLR or LRP.

"ApoB100" or "apoliprotein B100" refers to the 514 glycoprotein on the surface of the naturally occurring LDL. This lipid binding protein is very large and consists of a hydrophobic domain, amphipathic beta sheets and amphipathic α-helices. A protein sequence of the human apoB100 is identified by GenBank accession number NP 000375; which is the protein product of the nucleic acid sequence identified by GenBank accession number M15421.

"Therapeutic treatment" and "cancer therapies" and "cancer therapy reagents" refers to apoptosis-mediated and non-apoptosis mediated cancer therapies that treat, prevent, or inhibit cancers, including chemotherapy, hormonal therapy (e.g., androgens, estrogens, antiestrogens (tamoxifen), progestins, thyroid hormones and adrenal cortical compounds), radiotherapy, and immunotherapy.

"Cancer" or "carcinoma" refers to a number of human illnesses including sarcomas, adenocarcinomas, choriocarcinoma, lymphomas, leukemias, etc., including solid and lymphoid cancers, kidney, breast, lung, bladder, colon, ovarian, prostate, pancreas, adrenal gland, stomach, brain, head and neck, skin, uterine, testicular, glioma, glioblastoma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas) and Hodgkin's lymphoma, leukemia (including AML, ALL, and CML), multiple myeloma, mantle cell lymphoma, Waldenstrom's macrogobulinemia, and Philadelphia positive cancers.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Material and Methods

Low Density Lipoprotein. Human LDL was isolated from apheresis plasma of patients with familial hypercholesterolemia using sequential density gradient ultracentrifugation as described previously by Lund-Katz et al. (Lund-Katz et al., 1998).

Preparation of LDL-DHA. Incorporation of DHA (Nuchek Prep, INC) into LDL was performed by the reconstitution (coreloading) method (Krieger, 1986). Briefly, lyophilized LDL was subjected to organic extraction with heptane. Following the extraction, DHA was added to the LDL residue and the sample was allowed to sit at 4° C. for 90 min. Thereafter, heptane was removed by evaporation and the dried residue was resuspended in Tricine buffer. After an overnight incubation at 4° C., LDL samples were clarified by low-speed centrifugation and stored under $N_2$ atmosphere at 4° C. Control LDL Nanoparticles: Throughout these studies, various LDL particles were used as controls. These included native LDL as an overall control vehicle; LDL reconstituted with oleic acid (LDL-OA), or LDL reconstituted with oleic acid triglyceride (triolein) (LDL-TO).

Preparation of HAS-DHA. Human serum albumin (HSA; 5% w/v) was dissolved in 1 ml of 75 mM KCl solution and pH was adjusted to 7.4. DHA in ethanol (0.125% w/v; final concentration) was added to HSA solution, vortexed briefly and incubated at 37° C. for 1 hour. Samples were then filtered through 0.2 nm syringe filter and stored at 2-8° C. until further use.

Structure and composition. The morphology and structure of the LDL particles was visualized with negative stain and transmission electron microscopy (FEI Tecnai G2 Spirit Biotwin electron microscope). The composition of the LDL nanoparticles were assayed for phospholipids (Wako), free and esterified cholesterol (BioVision), free fatty acids and triglycerides (reverse phase-HPLC) (Mehta et al., 1998) and protein (Bradford protein assay kit-Sigma). Molar concentrations of each component per particle were determined based on the assumption that one copy of the ApoB-100 protein is present per LDL particle.

Percent recovery and loading. Percent recoveries were determined by comparing the amount of DHA actually incorporated into LDL with the initial DHA used, as follows:

Percent recovery (%)=Actual DHA content in LDL (mg)/total DHA used (mg)×100

Mean particle size, polydispersity index and zeta potential. The size distribution and polydispersity indices (PDI) of LDL nanoparticles were evaluated by dynamic light scattering measurements at 25° C., and the zeta potential was measured in phosphate buffer at pH 7.4 using a Zetasizer Nano (ZEN3500, Malvern Instruments, UK). All measurements were performed at least in triplicates.

Turbidity measurement. Change in turbidity was determined by measuring light transmission through LDL and LDL-DHA samples at 600 nm using UV-visible spectrophotometer (UV 1800, Shimadzu, USA). Samples were vortexed prior to analysis. A reduction in transmission indicated an increase in turbidity.

Apoprotein secondary structure. Far-UV circular dichroism (CD) spectroscopy of LDL nanoparticles were recorded using a Jasco J-810 CD spectrometer. The CD spectra were recorded at 25° C. with a 1 nm step size from 260 to 195 nm. The data was collected over three consecutive scans and averaged. Readings were normalized to protein concentration and expressed as molar ellipticity. Estimates of ApoB-100 protein secondary structure was determined using Dichroweb CDSSTR software package.

Agarose electrophoresis. The electrophoretic properties of LDL particles were examined by 1.0% agarose gel electrophoresis. Samples (10 µg) were applied to gel wells and allowed to penetrate into gel for 5 min before the electric field was applied. Electrophoresis was performed at a voltage of 130 V for 30 min at 25° C. in barbital buffer (pH 8.6, 0.05 ionic strength). After electrophoresis the migration of the LDL particles were visualized by Coomassie staining.

Physical stability of LDL nanoparticles. The physical stability of native LDL and LDL nanoparticles was investigated over a one month period under ambient room temperature and oxygen. Physical stability was assessed by measuring particle size, PDI, zeta-potential, turbidity and protein secondary structure (CD). Phospholipid, protein and DHA contents of the LDL particles were also monitored during this time period.

Oxidative stability of LDL nanoparticles. The oxidative stabilities of native LDL and LDL nanoparticles were investigated at different storage conditions: (i) room temperature for 1 month; (ii) 40° C. for four days; and (iii) 55° C. for 5 hrs. All samples (50 µl) were vortexed thoroughly in a mixture of 700 µl $CHCl_3$:MeOH (2:1 v/v) and 250 µl of Milli-Q water. The chloroform layer was isolated by centrifugation and dried off under nitrogen. The dried residue was re-dissolved in a mixture of hexane, ammonium thiocyanate solution (30% w/v in water), freshly prepared ferrous chloride (0.4% w/v in 3.7% HCl) and ethanol (0.038: 0.02:0.02:1 v/v) under $N_2$ atmosphere. Absorbance of red color formed from the presence of ferric ion was measured at 500 nm using UV-visible spectrophotometer (UV 1800, Shimadzu, USA) and the concentration was determined using a calibration curve of ferric chloride ($FeCl_3$). All the reagents and solvents were deoxygenated by flushing with nitrogen prior to use. The peroxide value was calculated using the following formula:

$$PV=[Fe3+]/(55.84 \times g \text{ of lipids} \times 2)$$

where 55.84 is the molecular weight of iron. Results were expressed as mEq peroxide/kg lipid.

Cell culture. The mouse liver cell line TIB-73 (BNL CL.2) and its malignant counterpart TIB-75 (BNL 1MEA.7R.1) were obtained from ATCC (Manassas, Va.) and cultured in Dulbeco's modified Eagle's medium (DMEM) supplemented with 10% fetal bovine serum (FBS). Cells were grown at 37° C. in an atmosphere of 5% $CO_2$ in a humidified incubator.

Immunoblot. Whole cell lysates were separated on a 10% sodium dodecyl sulfate polyacrylamide gel and transferred to nitrocellulose. Membranes were then probed with anti-LDL receptor (LDLR) antibody kindly provided by Dr. Joachim Herz.

Binding and internalization of LDL and LDL-DHA. LDL-DiI and LDL-DHA-DiI were prepared according to the method of Pitas et al. (Pitas et al., 1981). For all of the binding and uptake studies the cells were incubated with serum-free DMEM media overnight prior to the start of experiments. For the binding assays, cells were incubated with LDL-DiI/LDL-DHA-DiI (10 µg/ml) in serum-free DMEM culture medium for 2 hours at 4° C. Because receptors are not internalized at 4° C., only binding of the ligand to the cell surface receptors is measured. After washing with PBS, 1 mL of isopropanol was added to each well and the plates were rocked for 15 minutes in the dark. The isopropanol extract of DiI was transferred to a tube and centrifuged for 15 minutes at 3000 rpm. Thereafter, the DiI fluorescence signal was determined using a spectrofluorometer (excitation of 520 nm and an emission scan from 530 nm to 630 nm). Cells were dissolved with Cell Lysis Reagent (1 g/L sodium dodecyl sulfate in 0.1 M NaOH) for protein determination. The calculated bound LDL-DiI in µg/mL was normalized to cellular protein in mg/mL. To determine nonspecific binding of LDL-DiI/LDL-DHA-DiI to the cells, an excess of unlabeled native LDL was included in the assay. Parallel experiments were performed at 37° C. to measure total association of LDL-DiI/LDL-DHA-DiI (bound and internalized) to the cells. The amount of internalized LDL particle was calculated by subtracting the 4° C. binding values from the measure of total association at 37° C. To quantify binding of LDL to TIB-73 and TIB-75 cells, the cells were incubated at 4° C. for 2 hours with incremental amounts of LDL-DiI. To determine nonspecific binding of LDL-DiI to the cells, an excess of unlabeled native LDL was added. The specific binding was calculated by subtracting the nonspecific binding of DiI-LDL from the total binding. The curves generated by the specific binding data were transformed into a linear graph, according to the method of Scatchard using GraphPad Prism 6 software. The ordinate of the Scatchard plots (bound/free) represents the amount of specifically bound ligand (µg of protein/mg cellular protein) divided by the concentration of unbound ligand in the reaction mixture (µg of protein/ml). The dissociation constants (Kd) (slope) and the maximum binding capacity (Bmax) (x-intercept) were calculated using the GraphPad Prism nonlinear regression algorithm for one site specific binding.

Cell toxicity assay (MTS). Each cell type was seeded in 96-well plates ($2\times10^3$ cells/well). After 48 hrs of culture, the cells received various concentrations of the LDL-DHA nanoparticles ranging from 0 to 100 µM (DHA). For controls (LDL-OA/TO) dosing went as high as 200 µM. At the end of the 72 hr treatment period, the cell viability was measured by the MTS assay as recommended by the manufacturer. In brief, 20 µL MTS solution was added to each well and cells were incubated at 37° C. for 4 hrs followed by absorbance readings at 490 nm. The relative cell viability is expressed as a percentage of the non treated controls.

Co-culture experiment. A hydrophobic pen (VWR Scientific) was used to divide the wells of a sterile 6-well tissue culture plate in half. To one half of the well, $4\times10^4$ TIB-73 cells (35 µL) were spread gently over the surface using a sterile pipette tip followed by $3.5\times10^4$ TIB-75 cells (35 µL) over the other half of the well. The cells were allowed to adhere for 15 minutes before gently adding an additional 2 ml of DMEM with 10% FBS media to the wells. Cells were incubated for 3 days to reach approximately 80% confluence. The cells were then incubated overnight in serum-free DMEM prior to the start of treatments. Cells were imaged before treatment, after 24 hours, and after 72 hours of treatment (60 µM LDL-DHA, LDL-TO, or DMEM) at 10× using the Zeiss Axiovert 100 inverted microscope attached to an Optronics Microfire camera. After 72 hours of treatment, the whole wells were also imaged at 0.63×0.8 magnification using the Zeiss Stemi SV 11 dissecting microscope attached to an Optronics Macrofire CCD camera.

Cell death assay. Seventy-two hours following LDL nanoparticle treatments (40 µM) (as described above) cells were stained with the Promokine Apoptotic/Necrotic Cells Detection Kit according to the manufacturers protocols. The annexin-V FITC and propidium iodide (PI) double staining method was used to provide readouts of apoptotic and necrotic cells, respectively. Cells were analyzed by fluorescent microscope (NIKON Eclipse E600 microscope (Nikon, Lewisville, Tex.)) and flow cytometric analysis (FACScan flow cytometer, Becton Dickson, Mountain View, Calif., USA).

Lipid peroxidation. The total amount of lipid peroxidation products formed in the cells was determined using the thiobarbituric acid (TBA) method (Erdahl et al., 1991).

Cellular reactive oxygen species. Cellular reactive oxygen species (ROS) contents were measured by incubating cells with 15 µM 5-(and -6)-carboxy-2',7'-dichlorodihydrofluorescein diacetate (carboxy-H2-DCF-DA) for 1 hour at 37° C. After incubation, cells were washed with PBS and intracellular ROS accumulation was quantified with fluorescence spectrometry (Hitashi F-7000 fluorescence spectrophotometer with excitation at 485 nm and an emission scan from 500-560 nm) or observed and photographed using fluorescence microscope (NIKON Eclipse E600 microscope (Nikon, Lewisville, Tex.)) operating with a green filter set.

Statistical evaluation. The results were expressed as mean±standard error. Analysis of variance (ANOVA) with Tukey's multiple comparison post hoc testing was used for evaluation of differences between groups. Differences with a P value less than 0.05 were deemed significant.

EXAMPLE 2

Low-density Lipoprotein Mediated Delivery of Docosahexaenoic Acid Selectively Kills Murine Liver Cancer Cells Nanoparticle characterization. Replacement of the cholesteryl ester/triacylglycerol core of plasma LDL with DHA, as described by the reconstitution method, yields LDL particles that are uniformly loaded with DHA (FIG. 1A). Compositional analysis (Table 1) shows that on average for each LDL-DHA nanoparticle (given one copy of apoprotein B-100 per LDL) 390 phospholipid molecules make up its amphipathic monolayer shell while 1453 molecules of DHA pack its interior. LDL-DHA does not contain any free unesterified cholesterol, as is seen in the surface of native LDL. Free cholesterol along with the core neutral lipids are extracted from the LDL particle during the reconstitution process (Krieger et al., 1979). The efficiency of the reconstitution reaction was evaluated and was found to produce the LDL-DHA nanoparticle with good yield. The percent protein and DHA recovery from the initial starting materials were 46% and 13%, respectively. In addition, the average lipid (DHA) to protein mass ratio was calculated to be 0.82. These recovery values are in keeping with those cited in the seminal work by Krieger et al. (Krieger et al., 1979).

TABLE 1

Composition and physiochemical properties of native LDL and LDL nanoparticles.

|  | Native LDL | LDL-TO | LDL-OA | LDL-DHA |
|---|---|---|---|---|
| ApoB-100 | 1 | 1 | 1 | 1 |
| Phospholipid | 734 ± 114 | 862 ± 173 | 373 ± 79.7 | 386 ± 113 |
| Cholesterol* | 2958 ± 378 | ND | ND | ND |
| Lipid cargo | ** | 344 ± 26.6 | 1401 ± 371 | 1453 ± 92 |
| Diameter | 18.2 ± 0.3 | 20.3 ± 0.7 | 20.0 ± 0.9 | 18.3 ± 0.5 |
| Surface charge | −8.3 ± 0.7 | −15.0 ± 2.5 | −26.7 ± 6.1 | −21.9 ± 3.3 |

*Total cholesterol includes cholesteryl esters and free cholesterol. Literature values indicate that LDL typically carries between 1300-1600 cholestryl esters and 500-600 free cholesterol molecules (Hevonoja et al., 2000; Shen et al., 1977).
** LDL also carries about 170 triglyceride molecules. DHA typically makes up only 1% of the total fatty acid composition of LDL (Quilliot et al., 2003).

Figure 1B:
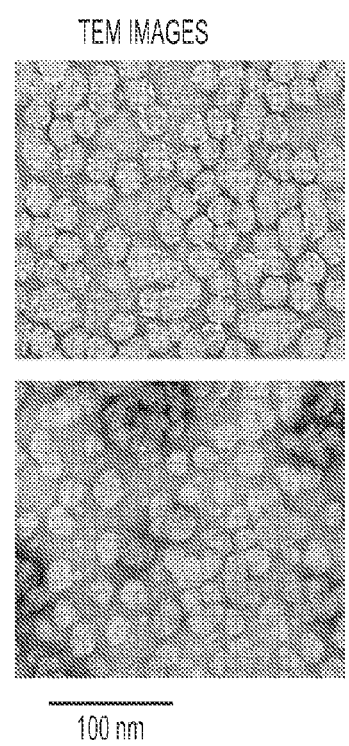
Figure 2A:
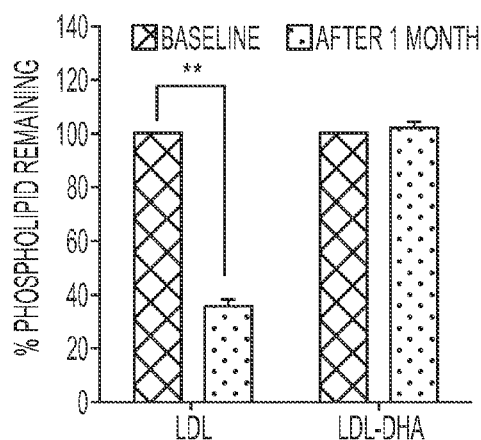
FIGS. 2A-C. Composition characterization and stability: All the samples were stored at ambient conditions and were subjected to composition analysis at baseline and at 1 month.
Figure 2B:
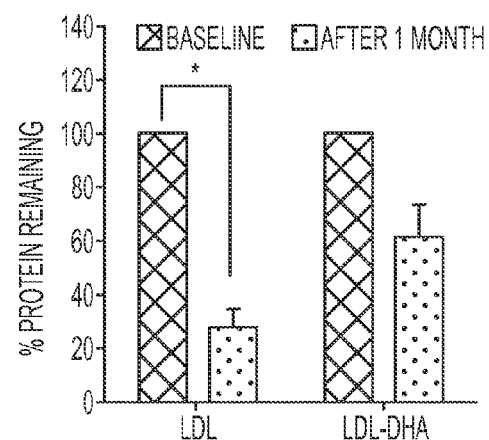
Figure 2C:
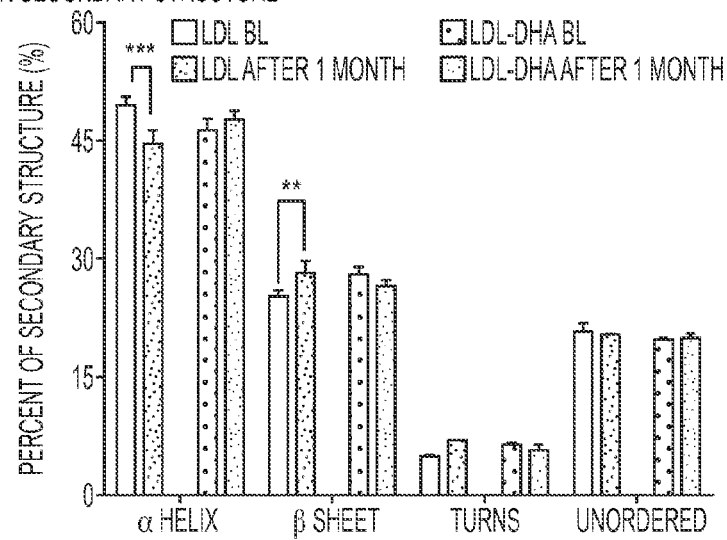

The LDL-DHA nanoparticle retains much of the structure and morphological features of native LDL. TEM micrographs (FIG. 1B) and DLS analyses reveal that the LDL-DHA consist of a fairly uniform population of quasispherical shaped particles with an average particle diameter of 18.3±0.53 nm (PDI=0.26). The other reconstituted LDL nanoparticles, LDL-OA and LDL-TO, also displayed similar size and morphology. The conformational structure of LDL-DHA apoB-100 was also monitored by CD spectrophotometry (FIG. 2C). The spectral secondary structure readings of apoB-100 in LDL-DHA indicate that it contains 46% α-helix, 28% β-sheet, 6% β-turns, and 20% unordered structure. The protein secondary structure of apoB-100 from native LDL had a similar conformation (49% α-helix, 25% β-sheet, 5% β-turns, and 21% unordered structure). The apoB-100 from LDL-OA and LDL-TO also contained a similar secondary conformation.

Figure 3A:
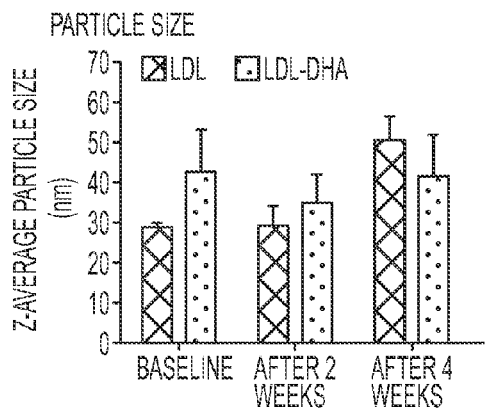
FIGS. 3A-D. Physicochemical properties and stability: All the samples were stored at ambient conditions and were subjected to physicochemical analysis at baseline, 2 weeks, and 4 weeks.
Figure 3B:
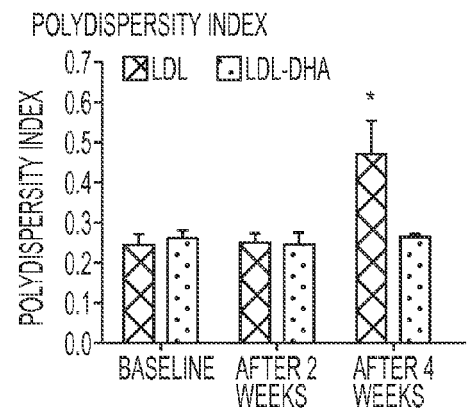
Figure 3C:
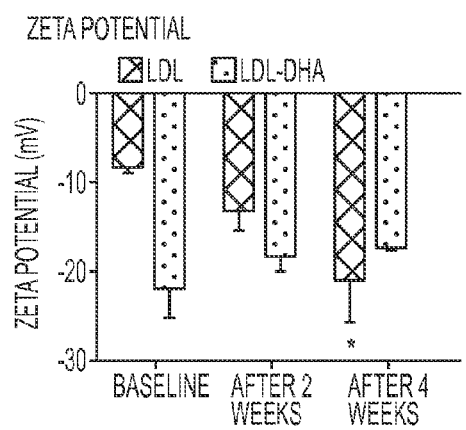
Figure 9:
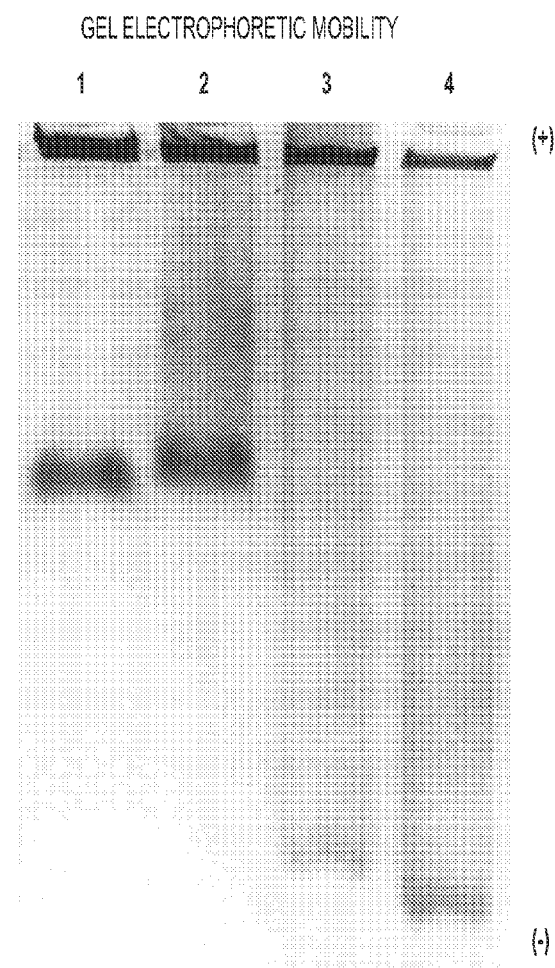
FIG. 9. Agarose gel electrophoresis of native LDL and reconstituted LDL nanoparticles. 1. Native LDL; 2. LDL-TO; 3. LDL-OA; 4. LDL-DHA.

The zeta-potential measure of surface charge for LDL-DHA differed considerably from native LDL (−22 mV and −8 mV, respectively) (FIG. 3C). These findings were confirmed by agarose gel electrophoresis as LDL-DHA showed a marked increase in its electrophoretic mobility (FIG. 9). Interestingly LDL-OA also displayed a strong electronegative surface charge and electrophoretic mobility while LDL-TO possessed values similar to native LDL.

Figure 3D:
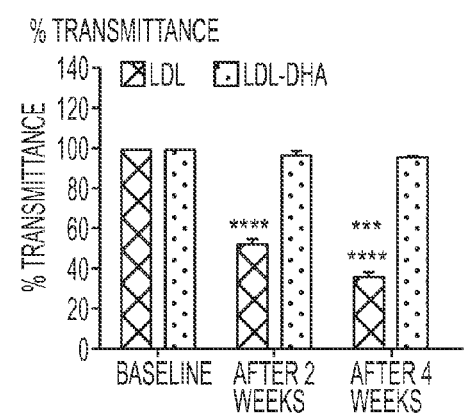

Stability experiments. The physicochemical stability of LDL-DHA and native LDL was monitored over a one month period under ambient conditions (room temperature and air). LDL-DHA showed notable stability across all the physicochemical parameters: the phospholipid and DHA content remained unaltered and showed no signs of leakage (FIG. 2A and FIG. 4A), the z-average particle size, PDI, % transmittance and zeta potential were similarly unchanged (FIGS. 3A-D) and the composition of the apo B-100 secondary structure was preserved (FIG. 2C). The apo B-100 protein content did decrease on average by 37% in the LDL-DHA samples, however, this drop was not deemed significant. Conversely, native LDL particles displayed pronounced degradative changes over this period. The content of apo B-100 protein decreased by 75% and its secondary structure composition was significantly altered (FIG. 2B). Similarly, the phospholipid content in native LDL also decreased by 63% (FIG. 2A). Significant flocculation of the native LDL occurred during this time, the Z-average particle size and PDI markedly increased, with a corresponding decrease in % transmittance (FIGS. 3A, 3B, 3D). The zeta potential of the native LDL also steadily increased over the 4 weeks (FIG. 3C).

Figure 4B:
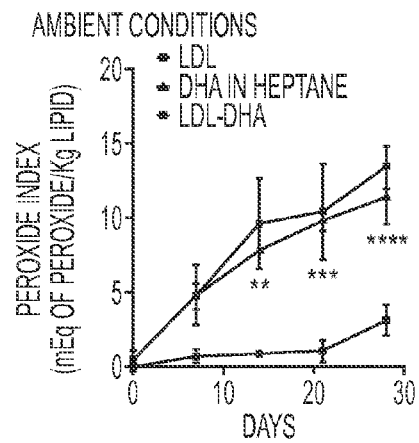
Figure 4C:
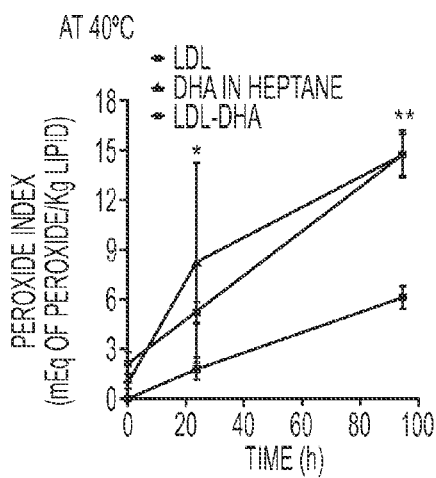
Figure 4D:
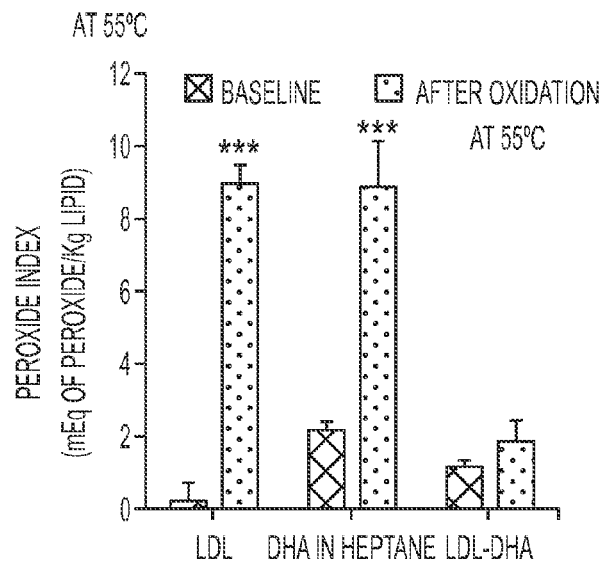

Next the oxidative stability of LDL-DHA, DHA in heptane and native LDL was measured under ambient and elevated stress conditions (FIGS. 4A-D). For the samples maintained at ambient room temperature and air for one month: the concentration of DHA in heptane decreased by 43%, accompanied by a sharp increase in the peroxide index (12 mEq/kg lipid). Over this time period, native LDL also showed a sharp rise in its peroxide index (14 mEq/kg lipid). Under the same conditions, LDL-DHA experienced little peroxidation (3 mEq/Kg lipid increase) (FIG. 4B). These findings agree with the stable content of DHA in LDL over this time period (FIG. 4A). The stability of LDL-DHA was then further tested under conditions of enhanced stress. Each sample was kept under air at 40° C. for four days. During this stress test period native LDL and DHA in heptane experienced a drastic rise in peroxide indices (>13.0 mEq/kg lipid). Once again, the peroxidation process was significantly blunted in LDL-DHA, where peroxide levels only reached 5.5 mEq/kg lipid (FIG. 4C). In the final stress test, samples were incubated under air at 55° C. for 5 hrs. Even under these extreme conditions the oxidative stability of LDL-DHA was maintained. In contrast, native LDL and DHA in heptane succumbed to significant degradative peroxidation (FIG. 4D).

Figure 10:
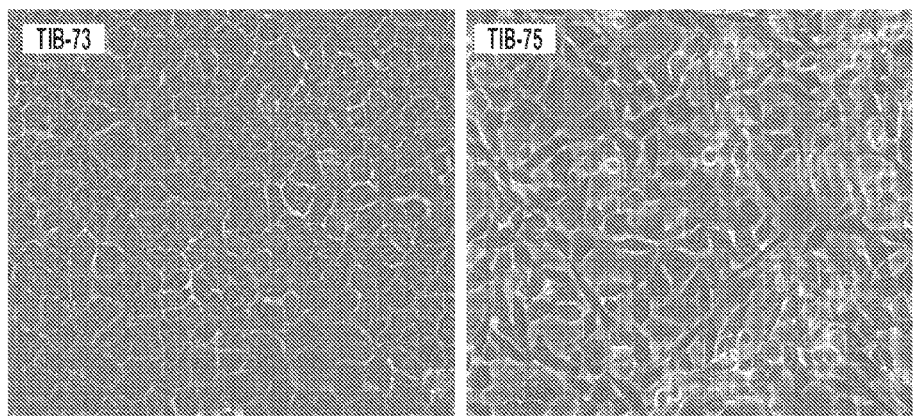
FIG. 10. TIB-73 and TIB-75 morphology. Bright field images of TIB-73 (left) and TIB-75 (right) morphology at 20× magnification.

Biological activity of LDL-DHA. The mouse liver cell lines, TIB-73 and TIB-75, displayed markedly different morphological features and patterns of growth (FIG. 10). The TIB-73 demonstrated more epithelial characteristics, as they grew as a monolayer in a 'cobblestone' pattern, similar to mature hepatocytes. The TIB-75, on the other hand, displayed more mesenchymal features. These cells grew in a more chaotic manner often forming multiple layers of cells.

Figure 5A:
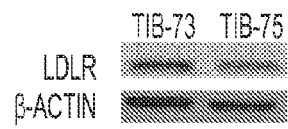
FIGS. 5A-D. Biological Activity of LDL-DHA.
Figure 5B:
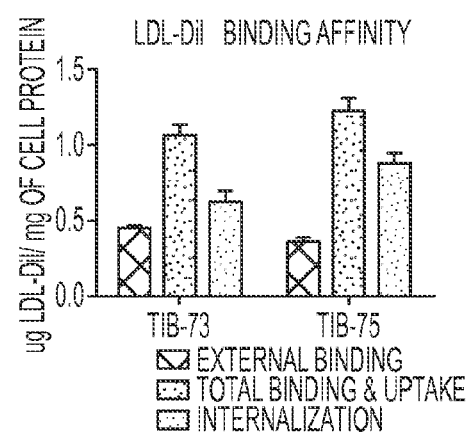
Figure 5C:
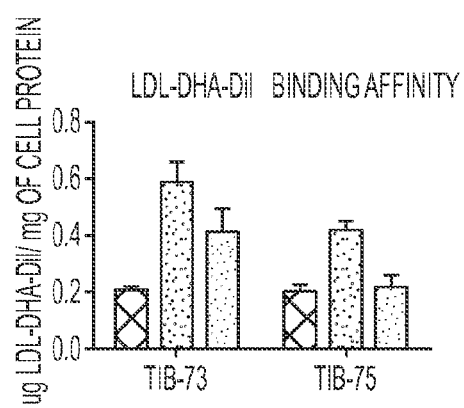
Figure 5D:
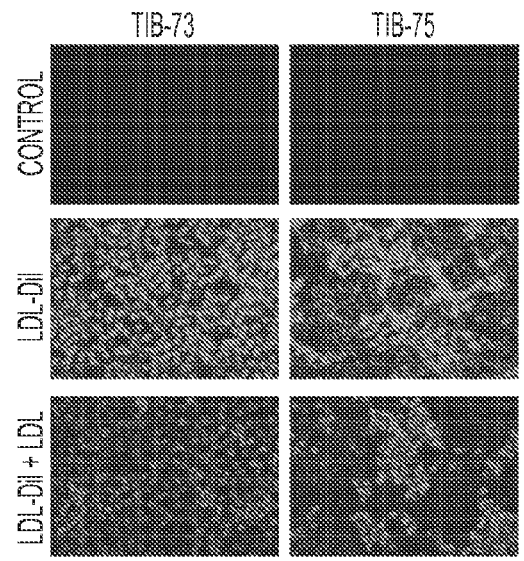
Figure 11A:
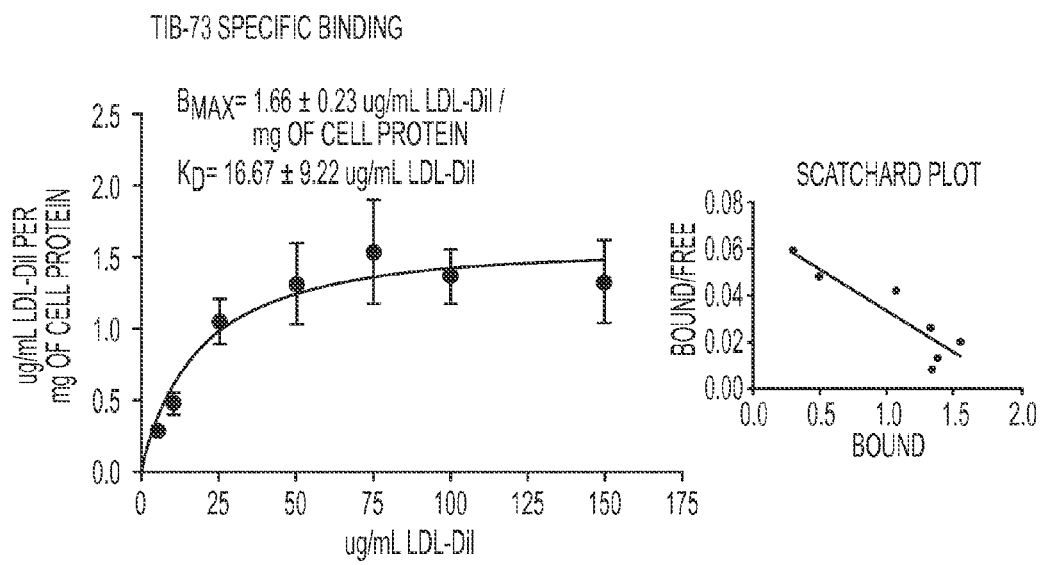
FIG. 11. LDL specific binding. TIB-73 and TIB-75 cells were treated in duplicate with LDL-DiI (0 to 150 μg/mL) with or without excess LDL (500 μg/mL) for 2 hours at 4° C. Following the incubation cells were washed and cellular DiI fluorescence (ex. 520 and em. 569 nm) and protein measurements were made. Values are expressed as μg LDL-DiI/mg of cell protein. The specific binding was calculated as the difference of the LDL-DiI+LDL from the LDL-DiI only treated cells. GraphPad Prism 6 software was used to calculate $K_D$ and $B_{max}$ and to generate the Scatchard Plot. Values represent the mean of four independent experiments.
Figure 11B:
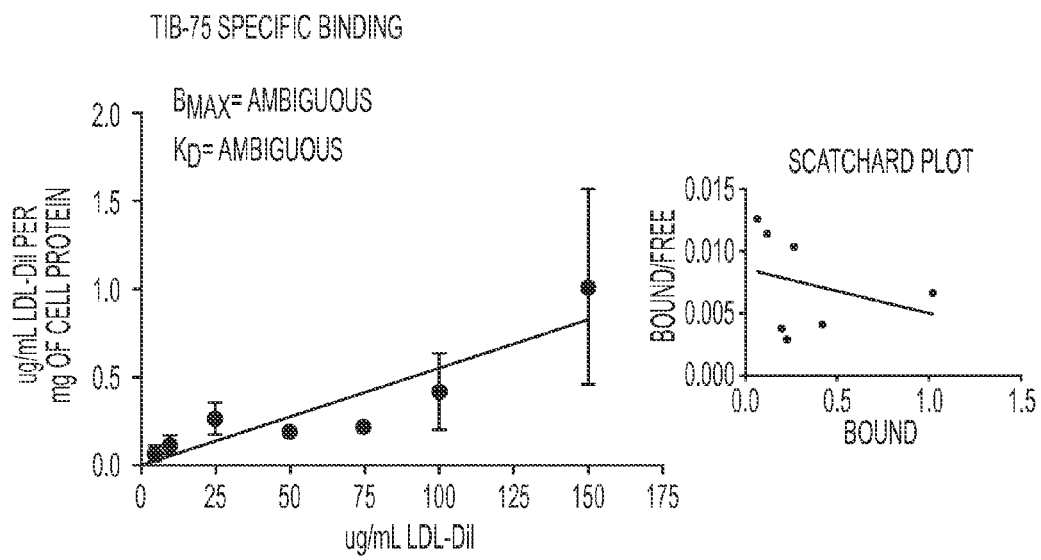
Figure 12:
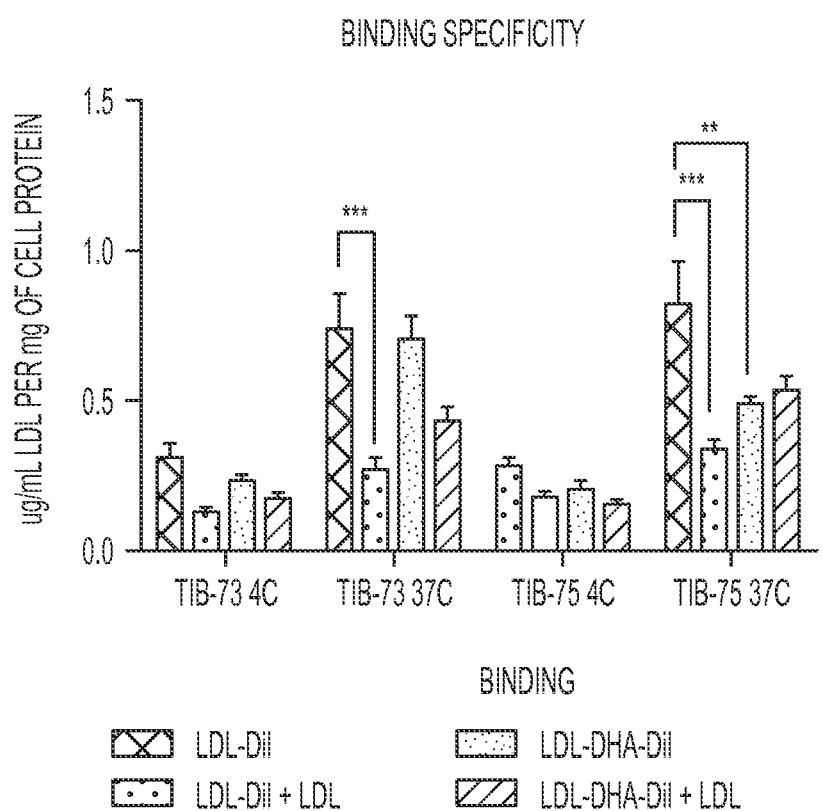
FIG. 12. Binding and specific uptake of LDL and LDL-DHA. TIB-73 and TIB-75 cells were treated in duplicate with either 10 μg/mL of LDL-DiI or LDL-DHA-DiI with or without excess LDL (500 μg/mL) for 2 hours at 4° C. or 37° C. Bars represent the relative external binding (4° C.) and total cell uptake (37° C.) of LDL-DiI and LDL-DHA-DiI normalized to cell protein. Values are the mean of four independent experiments. () $p<0.01$, (*) $p<0.001$.
Figure 13:
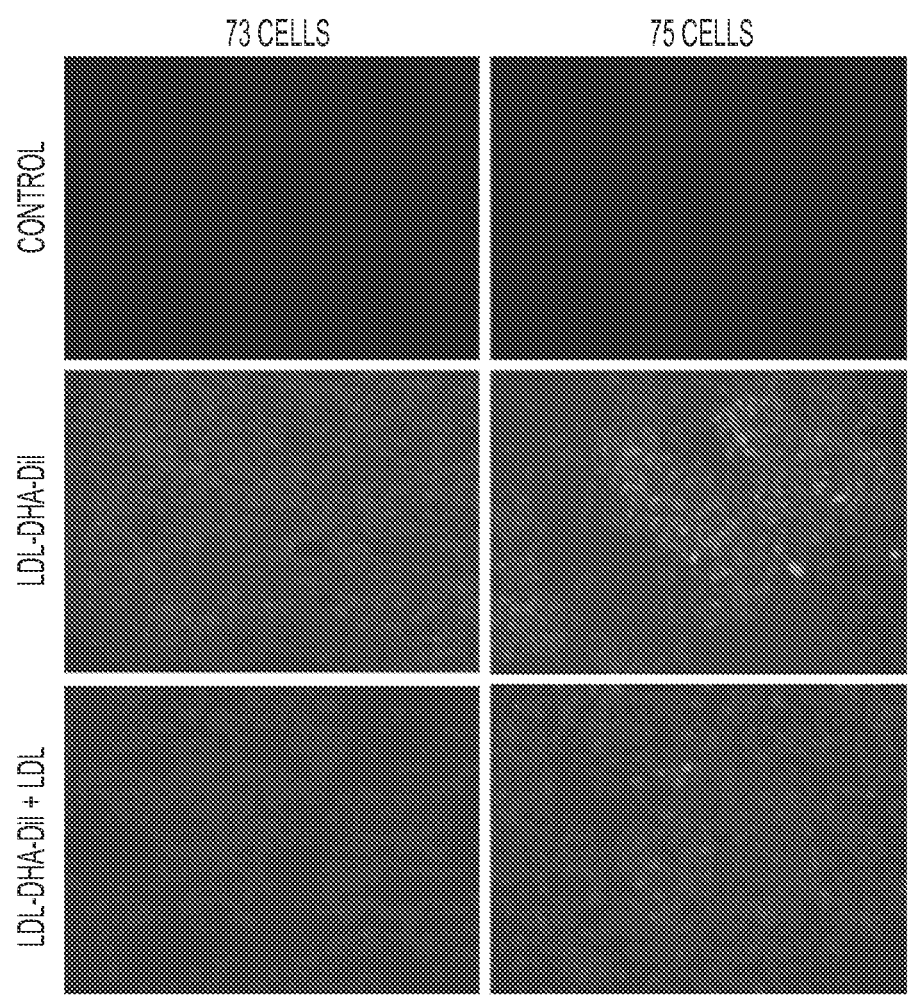
FIG. 13. Fluorescence Imaging of LDL-DHA Uptake. Fluorescent images (20× mag.) of TIB-73 and TIB-75 cells at baseline and following treatments with 10 μg/mL LDL-DHA-DiI or 10 μg/mL LDL-DHA-DiI+500 μg/mL LDL for 2 hours at 37° C.

Next the inventors examined how avidly TIB-73 and TIB-75 cells bind and take up LDL particles. Western blot analysis showed that TIB-73 cells expressed higher levels LDLR protein than TIB-75 cells (FIG. 5A). The LDLR binding assay showed that the TIB-73 cells bound and internalized LDL in a LDLR dependent manner ($K_D$=16.67±9.2 mg protein/ml LDL-DiI; $B_{max}$=1.66±0.23 μg LDL/mg cell protein) (FIG. 11 and FIG. 5C). Conversely, the TIB-75 cells bound LDL with non-saturable kinetics (FIG. 11). Additional uptake studies showed that TIB-75 was able to bind and internalize equal amounts of LDL as TIB-73 (FIG. 5B). The binding and uptake of LDL-DHA was similar to that of native LDL for each of the cells. TIB-73 continued to take up LDL-DHA in a LDLR dependent manner (FIG. 12). TIB-75 showed non-saturable and non-specific LDL-DHA binding. In addition, TIB-75 capacity for uptake and internalization of LDL-DHA was less than that of native LDL (FIG. 12 and FIG. 13).

Cytotoxicity experiments. The sensitivity of the liver cell lines to escalating concentrations of LDL-DHA nanoparticles was evaluated by the MTS assay (FIG. 6). LDL-DHA was immediately cytotoxic to the TIB-75 cells. The viability of these cells quickly declined with the initial doses of LDL-DHA (10 μM to 40 μM) and complete ablation of the TIB-75 cells was achieved at 60 μM LDL-DHA treatment. Conversely, LDL-DHA appeared to be innocuous to the TIB-73 over much of the dose response curve. In fact, the viability of the treated TIB-73 cells exceeded that of the baseline controls up to 70 μM LDL-DHA. It is not until LDL-DHA reaches concentrations exceeding 80 μM that the TIB-73 experience cytotoxic effects.

Figure 6A:
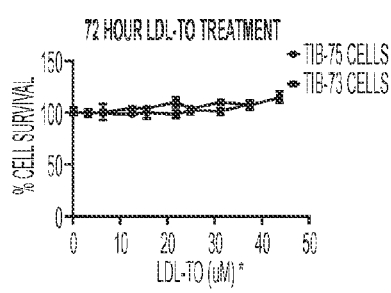
FIGS. 6A-D. LDL-DHA Anticancer Activity. TIB-73 and TIB-75 cells were treated for 72 hours with increasing concentrations of (FIG. 6A) vehicle control LDL-TO, (FIG. 6B) LDL-DHA, or (FIG. 6C) HSA-DHA. Following treatment, cell viability was determined by MTS assay where cell viability is normalized to the untreated cell controls.
Figure 6B:
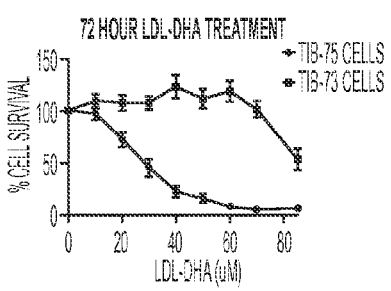
Figure 6C:
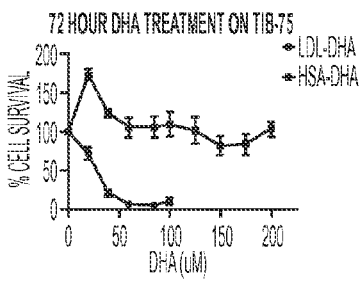
Figure 14:
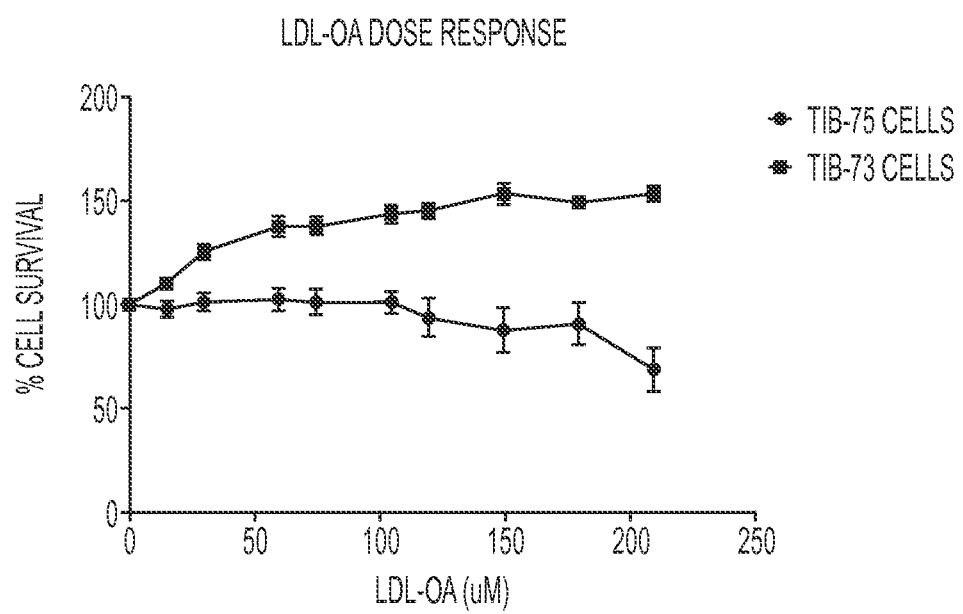
FIG. 14. LDL-OA viability assay. TIB-73 and TIB-75 cells were treated in triplicate with a dose range of LDL-OA (0 μM to 210 μM) for 72 hours. Cell viability was determined by MTS assay and normalized to the untreated cell controls.

The specificity of LDL-DHA toxicity towards malignant TIB-75 cells was confirmed with corresponding treatments of LDL-TO and LDL-OA (FIG. 6A and FIG. 14). MTS readings indicated that neither LDL-TO nor LDL-OA elicited significant cytotoxicity towards TIB-73 or TIB-75 cells over an equivalent dose range.

Figure 15:
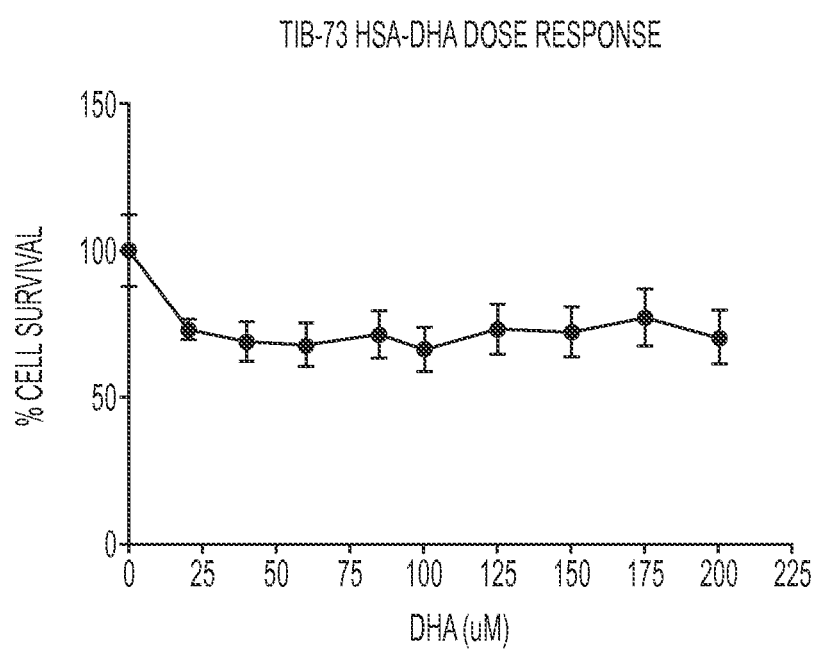
FIG. 15. HSA-DHA viability assay in TIB-73. TIB-73 cells were treated in triplicate with a dose range of HSA-DHA (0 μM to 200 μM) for 72 hours. Cell viability was determined by MTS assay and normalized to the untreated cell controls. Values represent the mean of five independent experiments.

Since albumin functions as one of the major transporters of free fatty acid in the plasma, the inventors decided to evaluate efficacy of HSA-DHA to kill TIB-75 cells (FIG. 6C). HSA-DHA failed to induce any toxicity in TIB-75 cells over an extended dose range up to 200 μM. Rather, the viability of TIB-75 was higher than that of untreated controls for most of the treatment doses of HSA-DHA. Interestingly, HSA-DHA treatment consistently compromised the viability of TIB-73 cells to 70% of the untreated controls over the entire dose range (FIG. 15).

Figure 6D:
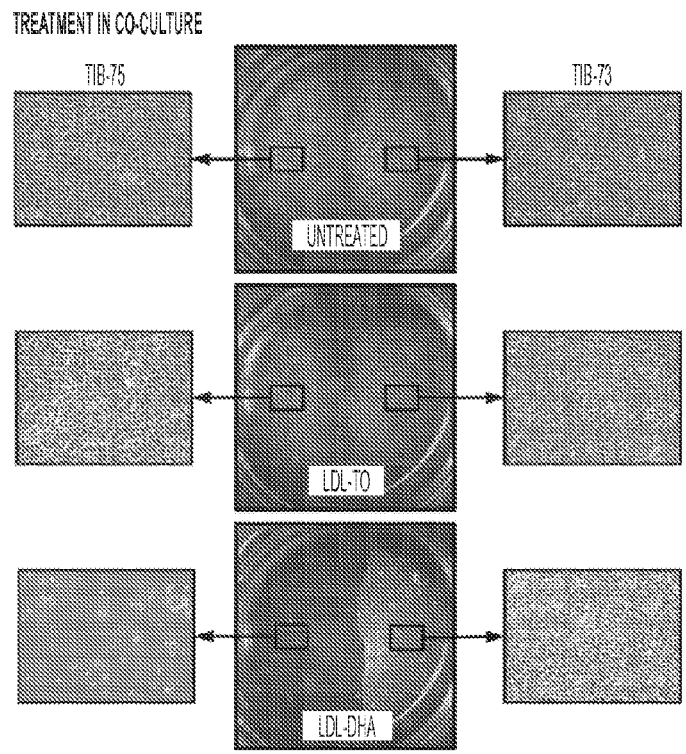
Figure 7A:
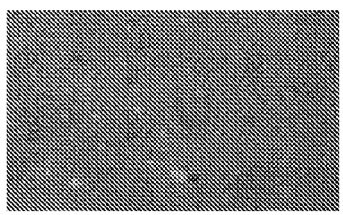
FIGS. 7A-G. Mode of cell death.
Figure 7B:
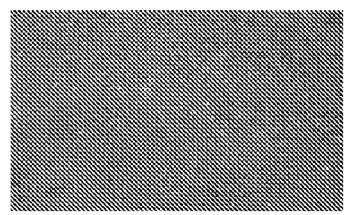
Figure 7C:
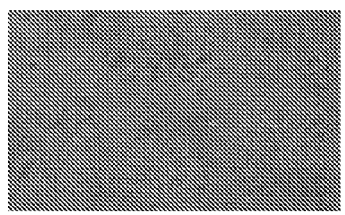
Figure 7D:
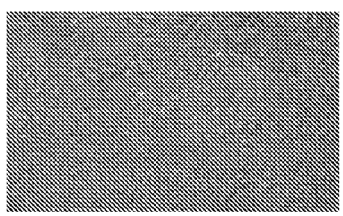
Figure 7E:
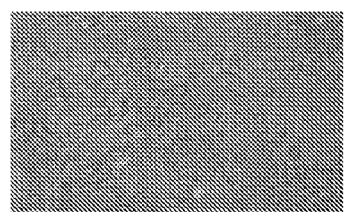
Figure 7F:
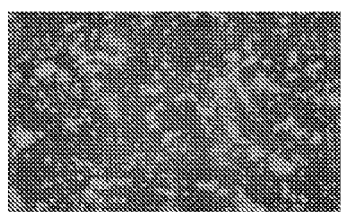
Figure 7G:
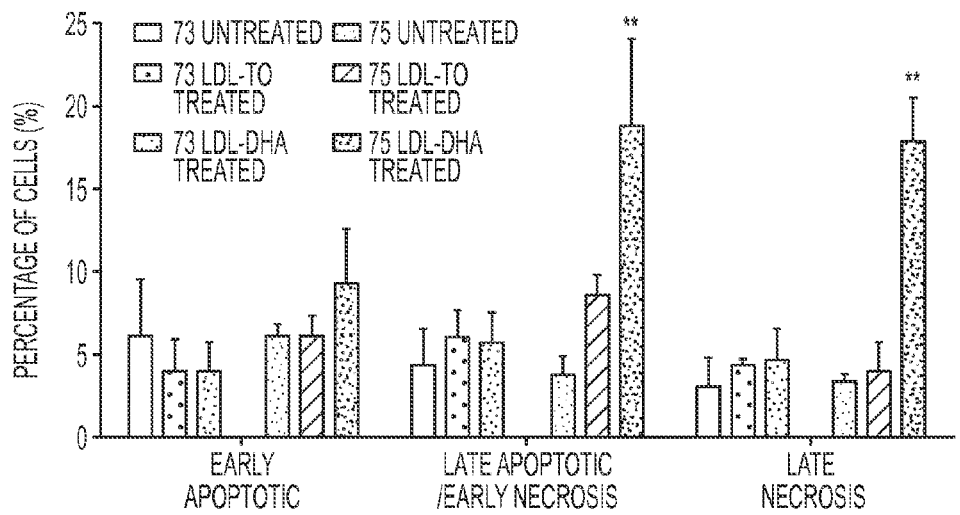

To further validate the MTS dose response findings, co-cultures of TIB-73 and TIB-75 were grown in 60 mm culture dishes (FIG. 6D). Over the duration of these experiments both cell types displayed their typical epithelial and mesenchymal phenotypes, respectively. As expected, treating the co-cultured cells with LDL-TO for 72 hrs did not hinder the proliferation of either cell type and both cells seemed to thrive under these conditions. In a similar manner, co-cultures of TIB-73 and TIB-75 were treated with LDL-DHA (60 μM). At the end of the treatment period TIB-73 cells did not experience any toxicity and continued to grow in their 'cobblestone' manner, filling much of their half of the culture dish. The TIB-75 cells had a much different fate, by the end of the 3 day incubation period they were completely killed. Only cell debris remained in the hemisphere initially occupied by TIB-75. Overall these findings were consistent with the MTS dose response studies and clearly demonstrated the selective cytotoxicity of LDL-DHA towards the malignant TIB-75 cells.

The effects of LDL-DHA on four additional malignant human hepatocellular cell lines was also examined (FIG. 18). LDL-DHA showed a dose-dependent effect on the cell viability of Huh7 (well differentiated), Focus (poorly differentiated; highly metastatic), HepG2 (hepatoblastoma), and Hep3B (well differentiated; Hep B background) cells.

Mode of cell death. To elucidate the specific cell death pathways elicited by LDL-DHA treatment, annexin-V-FITC and PI staining were performed in conjunction with flow cytometry and fluorescence microscopy (FIGS. 7A-G). FACS analysis showed that neither LDL-TO nor LDL-DHA treatments (60 μM) induced greater rates of apoptosis or necrosis in TIB-73 cells compared to what is normally seen in untreated controls (~5%-6%). This was also confirmed with fluorescence microscopy as the LDLTO and LDL-DHA treated TIB-73 images looked identical to the untreated TIB-73 group. For the TIB-75 cells, FACS analysis showed LDL-DHA treatment markedly activated both cell death pathways. TIB-75 cells showed significantly higher amounts of late apoptosis/early necrosis and late necrosis compared to all the other groups. This was also vividly demonstrated in the fluorescence microscopy images as LDL-DHA treated TIB-75 showed intense individual and coregistered staining of annexin-V and PI which was absent from the images of the other groups.

Figure 8A:
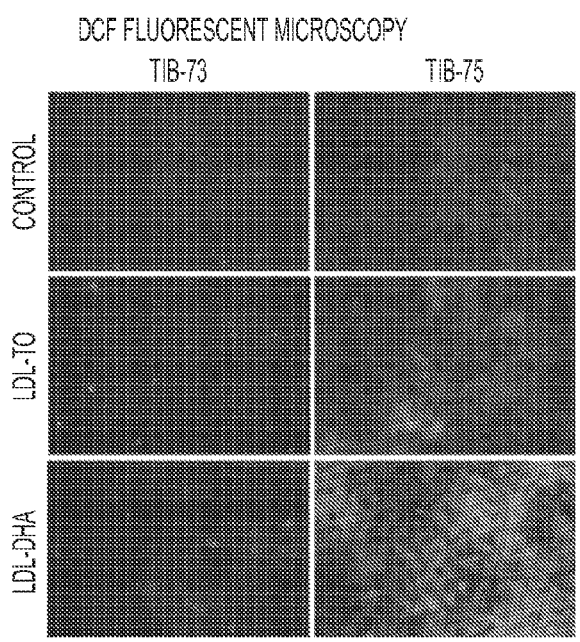
FIGS. 8A-D. Mechanism of Selective Cytotoxicity.
Figure 8B:
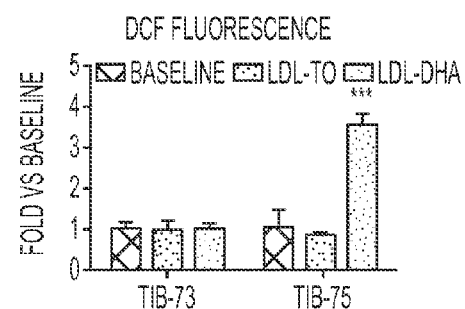
Figure 8C:
Figure 8D:
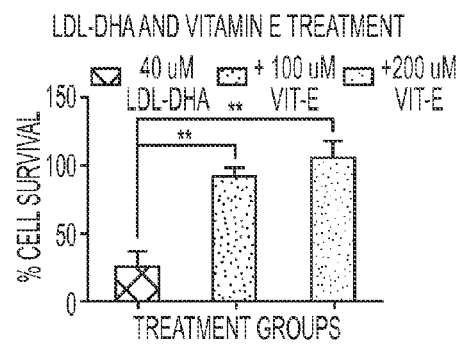

Mechanism of selective cytotoxicity. To investigate the mechanism of LDL-DHA selective toxicity, lipid peroxidation and the production of ROS were examined in the cells following treatment (FIGS. 8A-D). LDL-DHA treatment was shown to selectively induce both processes of lipid peroxidation and ROS in TIB-75 cells (FIGS. 8A-C). TBARS and DCF-DA-reactive species were significantly elevated 3-4 fold in the LDL-DHA treated TIB-75 cells. Neither biomarker was elevated in the TIB-73 cells following LDL-DHA treatment. An additional experiment later showed that co-incubation with the antioxidant, vitamin E, was able to effectively abrogate the cytotoxicity of LDL-DHA in TIB-75 cells (FIG. 8D). Collectively these findings support the central role of lipid peroxidation and ROS induction in the selective killing of malignant TIB-75 cells by LDL-DHA.

EXAMPLE 3

Figure 17:
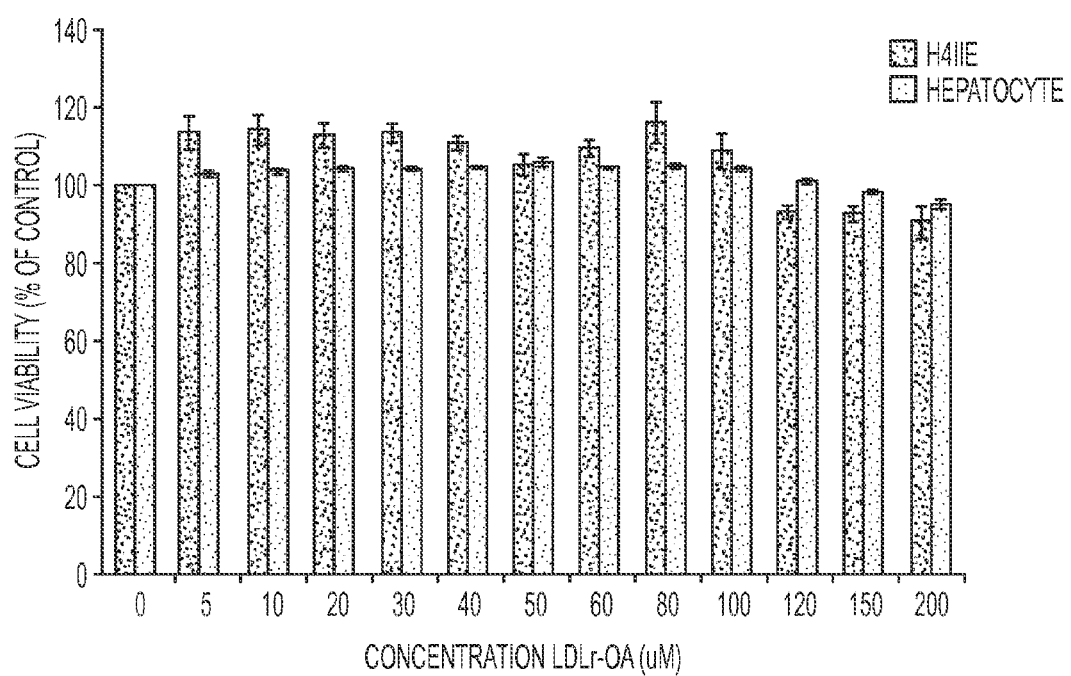
FIG. 17. Dose response of LDL-OA in primary rat hepatocytes and rat hepatoma cells. Cell viability (MTT assay) was performed following a 72 h incubation with LDL particles. Data are mean±standard error. Right columns are primary hepatocytes. Left columns are H4IIE cells.
Figure 22:
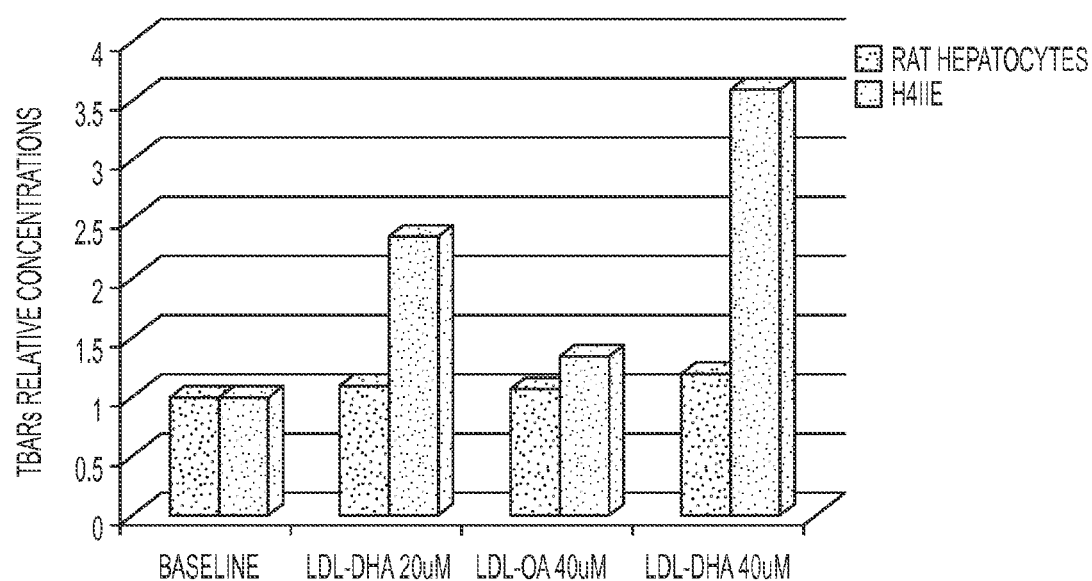
FIG. 22. Dose dependent induction of lipid peroxidation in rat hepatocytes and H4IIE cells. TBAR assays were performed 24 h following LDL-DHA treatment (30 μM). Left columns are rat hepatocytes; right columns are H4IIE cells.

In Vivo Studies of Low-density Lipoprotein Mediated Delivery of Docosahexaenoic Acid The dose response of LDL-DHA and LDL-OA in primary rat hepatocytes and rat hepatoma cells was examined (FIGS. 16 and 17). Cell viability assays were performed following a 72 h incubation with LDL particles. The LDL-DHA effect was specific to DHA (i.e., it was not a general effect of fatty acid). Also, the selective dose-dependent induction of lipid peroxidation was observed in H4IIE cells and not in rat hepatocytes (FIG. 22).

Figure 19:
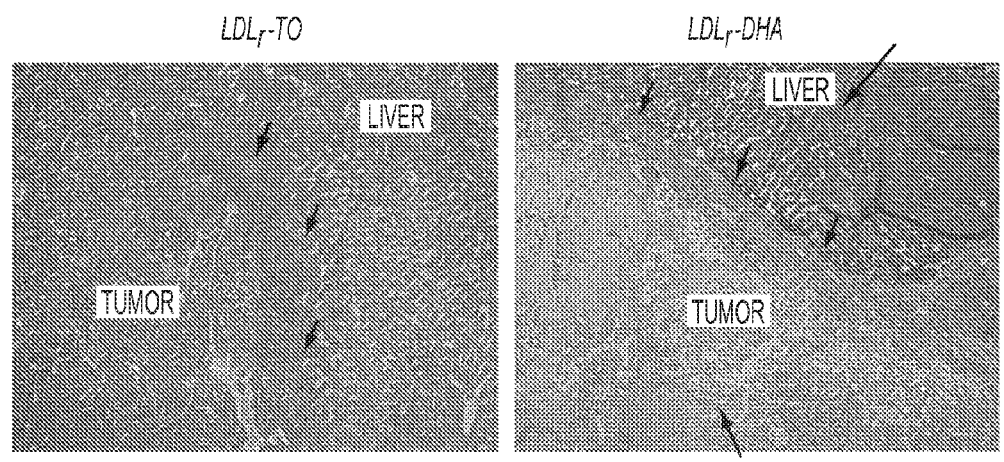
FIG. 19. Effects of LDL-DHA seven days following HAI in rat bearing orthotopic H4IIE hepatoma. LDL-TO was used as a negative control.

To generate a rat model of hepatocellular carcinoma, adult male ACI rats were injected with 2.5 millions H4IIE cells into the liver. Tumor formation was allowed to occur for 2 weeks and resulted in 1-2 cm$^3$ orthotopic hepatomas. The rats were treated with LDL-TO or LDL-DHA by hepatic artery infusion (HAI) and the effects of LDL-DHA were analyzed seven days following HAI. LDL-TO had no effect while LDL-DHA selectively resulted in complete necrotic destruction of the liver tumor (FIG. 19).

Figure 20:
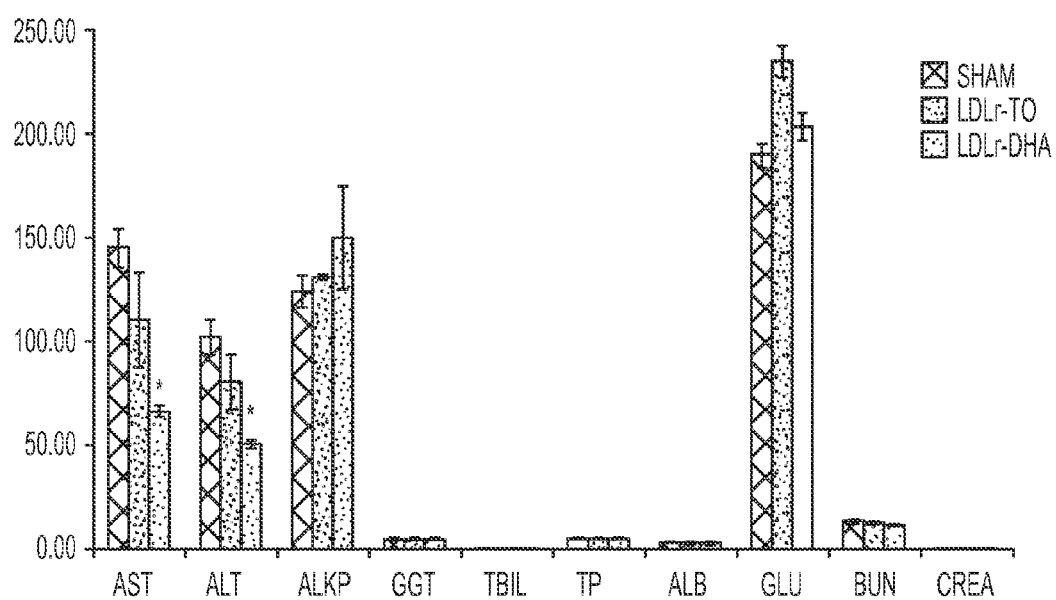
FIG. 20. Blood chemistry of tumor bearing rats seven days following HAI of LDL nanoparticles. LDL-DHA dose equivalent to 100 μM DHA. LDL-TO dose equal to LDL-DHA protein. Total protein, albumin, and globulin measured in g/dL. ALT and AST measured in IU/L. Total bilirubin, BUN, creatinine, and glucose measured in mg/dL. * significantly different from Sham and LDL-TO controls. Left columns are Sham; middle columns are LDL-TO; right columns are LDL-DHA.
Figure 21:
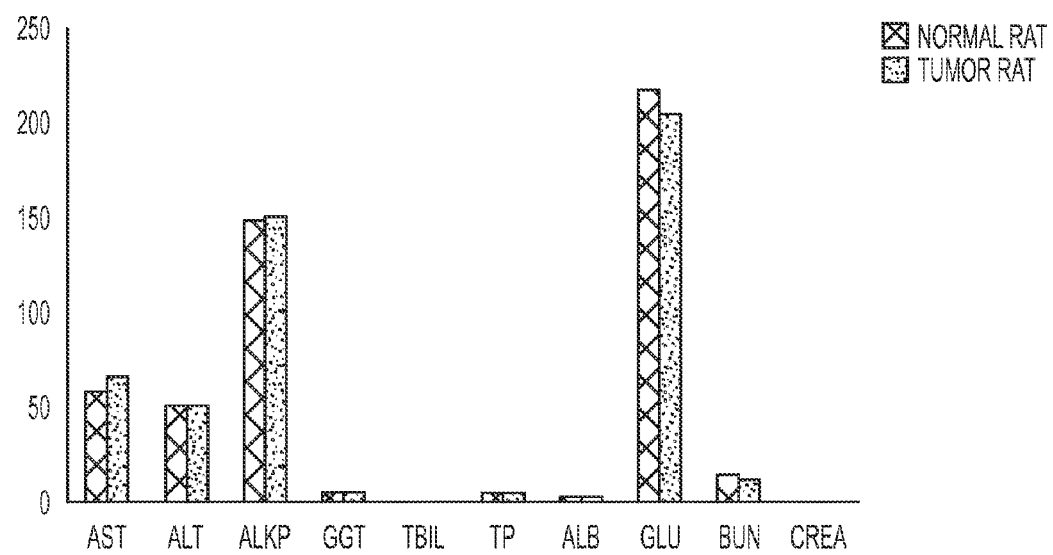
FIG. 21. Blood chemistry of tumor bearing and normal rats seven days following HAI of LDL-DHA nanoparticles. LDL-DHA dose equivalent to 100 μM DHA. Total protein, albumin, and globulin measured in g/dL. ALT and AST measured in IU/L. Total bilirubin, BUN, creatinine, and glucose measured in mg/dL. Left columns are normal rat; right columns are tumor rat.
Figure 23:
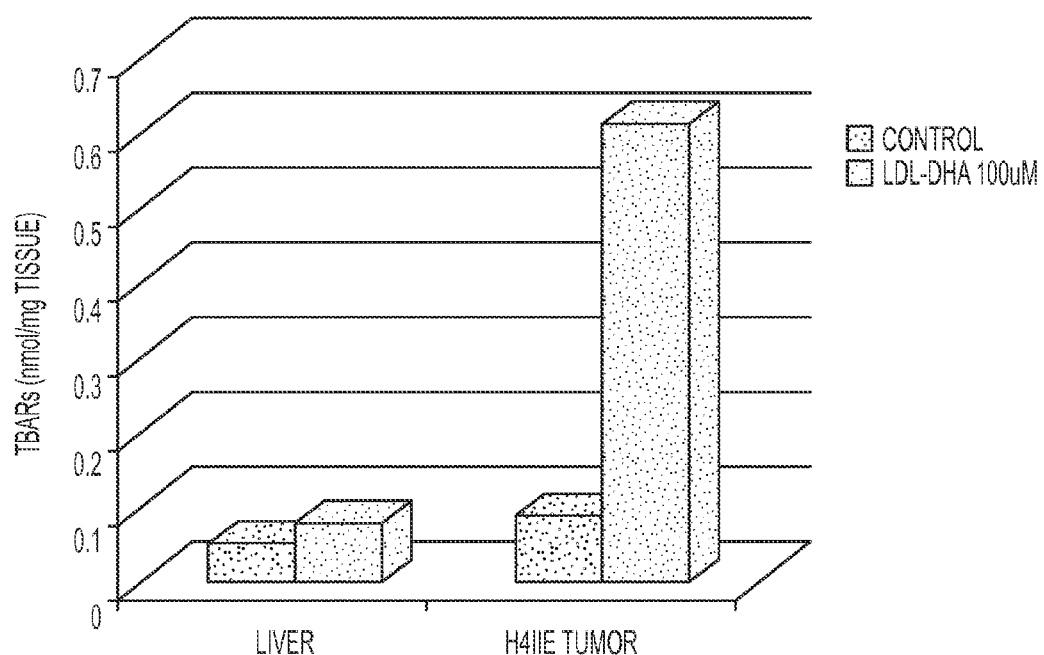
FIG. 23. Induction of lipid peroxidation in liver and tumor tissue following HAI LDL-DHA (100 μM). TBAR assays were performed seven days following HAI LDL-DHA treatment. Left columns are control; right columns are LDL-DHA 100 uM.
Figure 24:
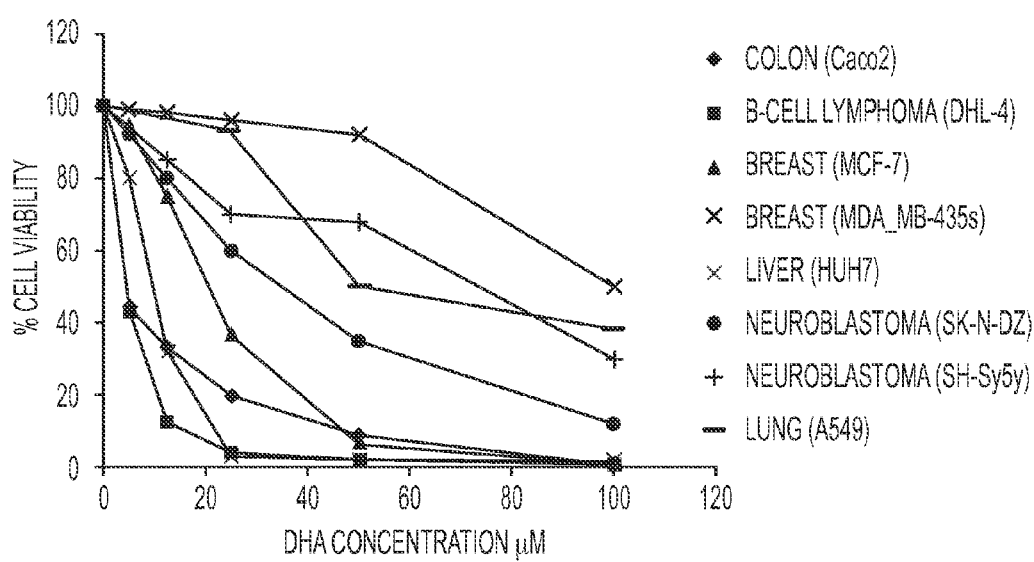
FIG. 24. Utility of DHA in other cancers. Dose response curves of DHA versus cell viability. Lines, from top to bottom at the 50 μM dose, represent Breast (MDA_MB-435s), Neuroblastoma (SH-Sy5y), Lung (A549), Neuroblastoma (SK-N-DZ), Colon (Caco2), Breast (MCF-7), Liver (HUH7), and B-cell lymphoma (DHL-4).

Blood chemistry of tumor bearing rats and normal rats was examined seven days following Sham surgery or HAI of LDL-TO or LDL-DHA nanoparticles (FIG. 20). The blood chemistry of the normal rat was also examined 7 days after HAI with LDL-DHA (FIG. 21). Normal rats displayed similar blood chemistry as tumor bearing rats after HAI treatment. In all cases there was no evidence of liver damage with LDL-DHA treatment. The induction of lipid peroxidation in liver and tumor tissue following HAI LDL-DHA was examined seven days following HAI of LDL-DHA (FIG. 23). Lipid peroxidation was selectively seen in H4IIE tumors and not in normal liver tissue.

Figure 25:
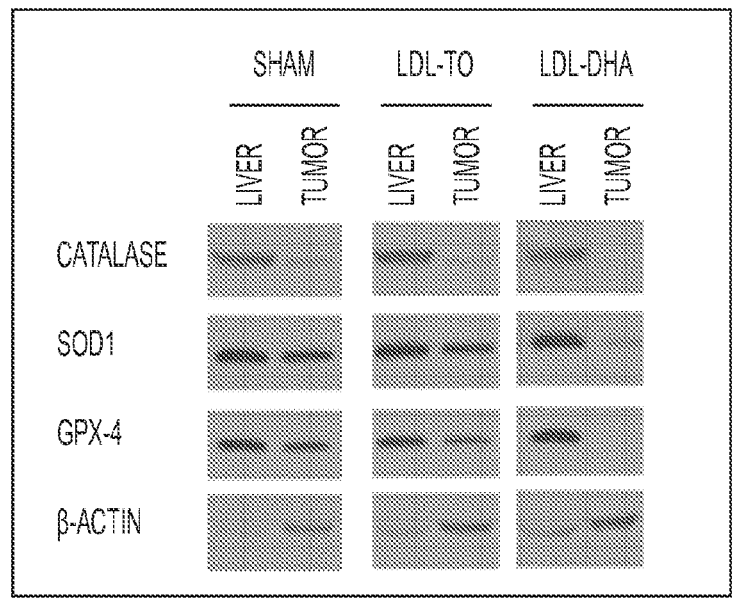
FIG. 25. LDL-DHA anticancer activity is mediate by selective disturbance of tumor redox balance. Protein expression levels of catalase, superoxide dismutase 1 and glutathione peroxidase 4 three days following Sham surgery or LDL nanoparticle treatments FIG. 26. LDL-DHA anticancer activity is mediate by selective disturbance of tumor redox balance. In vivo GSH: GSSG ratios in H4IIE tumor bearing rats 3 days following Sham surgery or LDL Nanoparticle treatment FIG. 27. Molecular mechanism studies for LDL-DHA anticancer activity. Protein expression levels of β-catenin, cyclinD1 and surviving 3 days following Sham surgery or LDL nanoparticle treatment.

Collectively, these studies show that hepatic artery infusion (HAI) of LDL-DHA selectively disrupts the redox balance in HCC tumors. Two sets of data that support this claim. First, the antioxidant enzyme system plays a key role in maintaining the intracellular balance between reduction and oxidative processes. When these enzymes malfunction or become depleted, catastrophic shifts in the cells redox balance can occur which can precipitate cell death. FIG. 25 shows that 3 days following HAI of LDL-DHA (100 μM) there is a selective depletion of catalase, superoxide dismutase 1(SOD1) and glutathione peroxidase 4 (GPX4) in the HCC tumor. With the significant reduction in these enzymes the HCC tumor becomes vulnerable to damaging oxidative processes.

Figure 26:
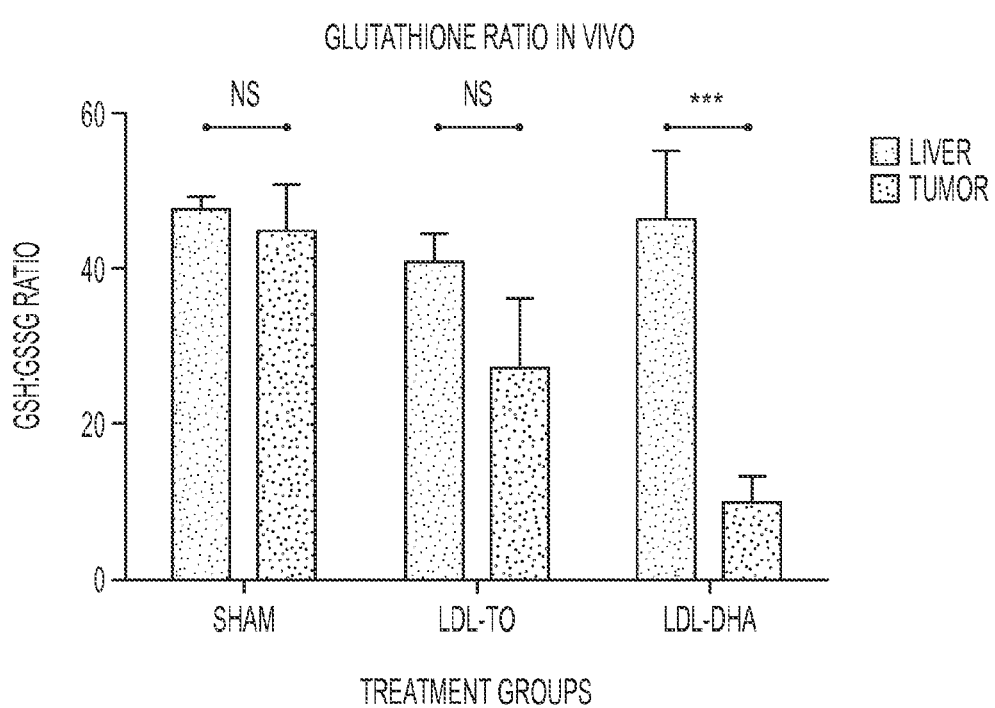

Second, Glutathione is another key molecule which enables cells to maintain a redox balance. Glutathione is normally present in high concentrations in the mammalian cell and is a major source of reducing equivalents. As such, it acts as a first line of defense against harmful free radicals. If oxidative events within the cell become too much for glutathione to buffer, the population of glutathione molecules will shift from a reduced state (GSH) to a more oxidized state (GSSG). LDL-DHA treatment selectively depletes the levels of reduced glutathione in the HCC tumor (FIG. 26). As the ratio of GSH:GSSG decreases the cell becomes more oxidized and prone to injury and cell/tissue death.

Figure 27:
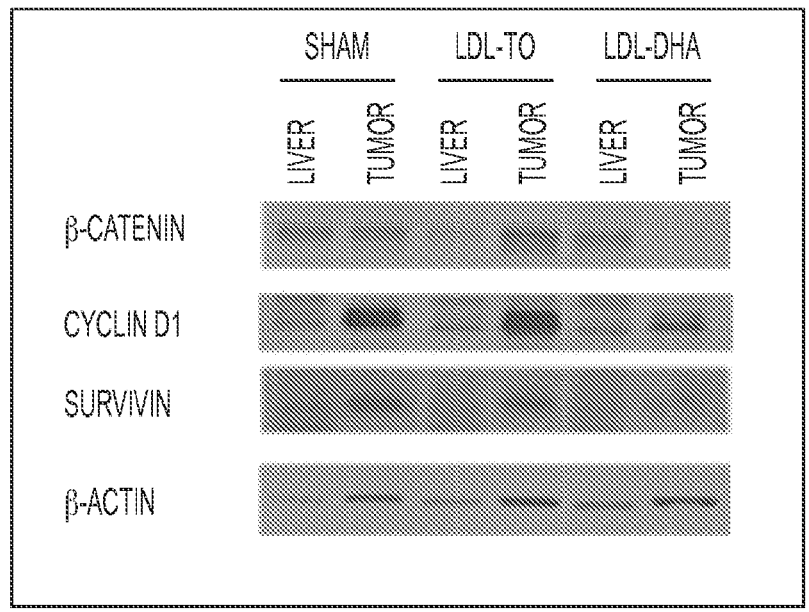

The Wnt/β-catenin pathway is a well-conserved pathway that is important in normal hepatic embryonic development, cell proliferation, survival, regeneration and self-renewal. Aberrant activation of this pathway has been found to play a major role in liver tumorigenesis and tumor progression by inciting downstream targets as c-Myc, cyclin D1, and survivin which promote tumor growth. Dysregulated Wnt/β-catenin activation is now recognized as a major marker in the molecular classification of HCC and is regarded to play a central role in the malignant phenotype of HCC. Thus, the Wnt/β-catenin pathway is viewed as a promising target for the treatment of HCC. Our early finding show that LDL-DHA treatment selectively reduces the β-catenin levels in HCC tumors which result decreased levels of downstream tumor promoting molecules cyclin D1 and survivin (FIG. 27).

Figure 28:
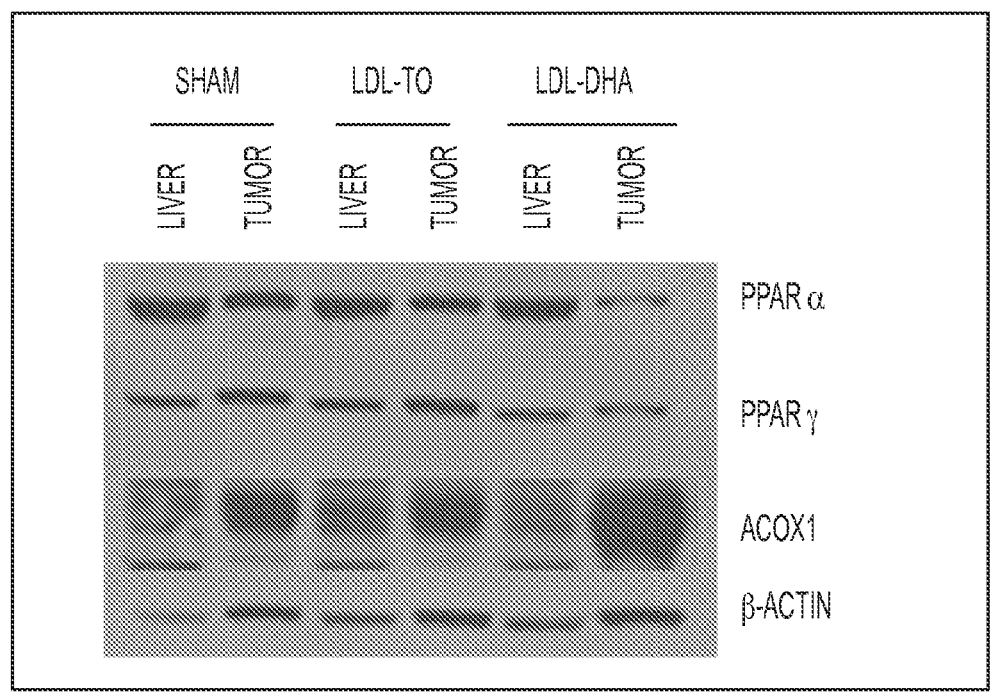
FIG. 28. Molecular mechanism studies for LDL-DHA anticancer activity. Protein expression levels of ppar$\alpha$, ppar $\gamma$ and ACOX1 3 days following Sham surgery or LDL nanoparticle treatment.

Peroxisome proliferator-activated receptors (PPARs) are members of the nuclear receptor superfamily of ligand-activated transcription factors. Upon ligand binding PPARs regulate numerous biological processes, which include lipid and energy metabolism, inflammation, cell differentiation, proliferation and death. Within the cancer biology field PPARγ and α have been most widely recognized as anti-cancer mediators and have been shown to induce apotosis in cancer cells. Moreover, DHA, is known to be able to activate PPARγ and α. Our preliminary in vivo data also confirm these findings (FIG. 28). Three days following HAI of LDL-DHA in H4IIE tumor bearing rats Western blot analysis of PPARγ, PPARα and acyl-CoA oxidase 1 (ACOX1)(an established PPAR target gene) show a pronounced increase of ACOX1 expression selectively within the H4IIE tumor; despite the moderate drops PPARγ and α expression within the tumor. This significant induction of ACOX1 is indicative of PPAR activation.

\* \* \*

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,186,183
U.S. Pat. No. 4,217,344
U.S. Pat. No. 4,235,871
U.S. Pat. No. 4,261,975
U.S. Pat. No. 4,485,054
U.S. Pat. No. 4,501,728
U.S. Pat. No. 4,529,561
U.S. Pat. No. 4,737,323
U.S. Pat. No. 4,774,085
U.S. Pat. No. 4,837,028
U.S. Pat. No. 4,946,787
U.S. Pat. No. 8,252,338
PCT Publication WO 91/17424
S. D. Hursting, M. Thornquist, M. M. Henderson, Prev Med, 19 (1990) 242-253.
C. P. Caygill, A. Charlett, M. J. Hill, Br J Cancer, 74 (1996) 159-164.
S. Sasaki, M. Horacsek, H. Kesteloot, Prev Med, 22 (1993) 187-202.
S. Sasazuki, M. Inoue, M. Iwasaki, N. Sawada, T. Shimazu, T. Yamaji, R. Takachi, S. Tsugane, Int J Cancer, 129 (2011) 1718-1729.
N. Sawada, M. Inoue, M. Iwasaki, S. Sasazuki, T. Shimazu, T. Yamaji, R. Takachi, Y. Tanaka, M. Mizokami, S. Tsugane, Gastroenterology, 142 (2012) 1468-1475.
I. M. Berquin, Y. Min, R. Wu, J. Wu, D. Perry, J. M. Cline, M. J. Thomas, T. Thornburg, G. Kulik, A. Smith, I. J. Edwards, R. D'Agostino, H. Zhang, H. Wu, J. X. Kang, Y. Q. Chen, J Clin Invest, 117 (2007) 1866-1875.
S. Iwamoto, H. Senzaki, Y. Kiyozuka, E. Ogura, H. Takada, K. Hioki, A. Tsubura, Nutr Cancer, 31 (1998) 143-150.
L. M. Braden, K. K. Carroll, Lipids, 21 (1986) 285-288.
D. P. Rose, M. A. Hatala, J. M. Connolly, J. Rayburn, Cancer Res, 53 (1993) 4686-4690.
K. S. Kang, P. Wang, N. Yamabe, M. Fukui, T. Jay, B. T. Zhu, PLoS One, 5 (2010) e10296.
K. Lim, C. Han, Y. Dai, M. Shen, T. Wu, Mol Cancer Ther, 8 (2009) 3046-3055.
M. Lindskog, H. Gleissman, F. Ponthan, J. Castro, P. Kogner, J. I. Johnsen, Int J Cancer, 118 (2006) 2584-2593.
J. A. Conquer, B. J. Holub, J Lipid Res, 39 (1998) 286-292.
H. Gleissman, L. Segerstrom, M. Hamberg, F. Ponthan, M. Lindskog, J. I. Johnsen, P. Kogner, Int J Cancer, (2010).
M. Noguchi, M. Minami, R. Yagasaki, K. Kinoshita, M. Earashi, H. Kitagawa, T. Taniya, I. Miyazaki, Br J Cancer, 75 (1997) 348-353.
M. V. Swamy, B. Citineni, J. M. Patlolla, A. Mohammed, Y. Zhang, C. V. Rao, Nutr Cancer, 60 Suppl 1 (2008) 81-89.
A. Gupta, C. S. Reilly, Continuing Education in Anaesthesia, Critical Care & Pain, 7 (2007) 148-151.
T. Namani, T. Ishikawa, K. Morigaki, P. Walde, Colloids Surf B Biointerfaces, 54 (2007) 118-123.
S. Kanno, K. Kurauchi, A. Tomizawa, S. Yomogida, M. Ishikawa, Toxicol Lett, 200 (2011) 154-161.
M. Roche, P. Rondeau, N. R. Singh, E. Tarnus, E. Bourdon, FEBS Lett, 582 (2008) 1783-1787.
K. Gura, 2006.
O. Lutz, Z. Meraihi, J. L. Mura, A. Frey, G. H. Riess, A. C. Bach, Am J Clin Nutr, 50 (1989) 1370-1381.
F. L. Oliveira, S. C. Rumsey, E. Schlotzer, I. Hansen, Y. A. Carpentier, R. J. Deckelbaum, JPEN J Parenter Enteral Nutr, 21 (1997) 224-229.
M. L. Hill, I. R. Corbin, R. B. Levitin, W. Cao, J. G. Mainprize, M. J. Yaffe, G. Zheng, Acad Radiol, 17 (2010) 1359-1365.
D. E. Marotta, W. G. Cao, E. P. Wileyto, H. Li, I. Corbin, E. Rickter, J. D. Glickson, B. Chance, G. Zheng, T. M. Busch, Nanomedicine-Uk, 6 (2011) 475-487.
T. Murakami, W. Wijagkanalan, M. Hashida, K. Tsuchida, Nanomedicine (Lond), 5 (2010) 867-879.
M. M. Shahzad, L. S. Mangala, H. D. Han, C. Lu, J. Bottsford-Miller, M. Nishimura, E. M. Mora, J. W. Lee, R. L. Stone, C. V. Pecot, D. Thanapprapasr, J. W. Roh, P. Gaur, M. P. Nair, Y. Y. Park, N. Sabnis, M. T. Deavers, J. S. Lee, L. M. Ellis, G. Lopez-Berestein, W. J. McConathy, L. Prokai, A. G. Lacko, A. K. Sood, Neoplasia, 13 (2011) 309-319.
T. Skajaa, D. P. Cormode, P. A. Jarzyna, A. Delshad, C. Blachford, A. Barazza, E. A. Fisher, R. E. Gordon, Z. A. Fayad, W. J. Mulder, Biomaterials, 32 (2011) 206-213.
P. Zhou, S. Hatziieremia, M. A. Elliott, L. Scobie, C. Crossan, A. M. Michie, T. L. Holyoake, G. W. Halbert, H. G. Jorgensen, J Control Release, 148 (2010) 380-387.
I. R. Corbin, K. K. Ng, L. Ding, A. Jurisicova, G. Zheng, Nanomedicine (Lond), (2012).
A. M. Gotto, Jr., H. J. Pownall, R. J. Havel, Methods Enzymol, 128 (1986) 3-41.
G. Favre, C R Seances Soc Biol Fil, 186 (1992) 73-87.
D. Gal, M. Ohashi, P. C. MacDonald, H. J. Buchsbaum, E. R. Simpson, Am J Obstet Gynecol, 139 (1981) 877-885.
Y. K. Ho, R. G. Smith, M. S. Brown, J. L. Goldstein, Blood, 52 (1978) 1099-1114.
S. Lund-Katz, P. M. Laplaud, M. C. Phillips, M. J. Chapman, Biochemistry, 37 (1998) 12867-12874.
M. Krieger, Methods Enzymol., 128 (1986) 608-613.
A. Mehta, A. M. Oeser, M. G. Carlson, J Chromatogr B Biomed Sci Appl, 719 (1998) 9-23.
R. E. Pitas, T. L. Innerarity, J. N. Weinstein, R. W. Mahley, Arteriosclerosis, 1 (1981) 177-185.
W. L. Erdahl, R. J. Krebsbach, D. R. Pfeiffer, Archives of Biochemistry and Biophysics, 285 (1991) 252-260.

M. Krieger, M. J. McPhaul, J. L. Goldstein, M. S. Brown, J Biol Chem, 254 (1979) 3845-3853.
R. E. Counsell, R. C. Pohland, J Med Chem, 25 (1982) 1115-1120.
M. Krieger, M. S. Brown, J. R. Faust, J. L. Goldstein, J Biol Chem, 253 (1978) 4093-4101.
R. A. Firestone, Bioconjug Chem, 5 (1994) 105-113.
A. Kader, P. J. Davis, M. Kara, H. Liu, J Control Release, 55 (1998) 231-243.
M. Masquelier, G. Tirzitis, C. O. Peterson, M. Palsson, A. Amolins, M. Plotniece, A. Plotniece, N. Makarova, S. G. Vitols, Eur J Med Chem, 35 (2000a) 429-438.
M. Masquelier, S. Vitols, M. Palsson, U. Mars, B. S. Larsson, C. O. Peterson, J Drug Target, 8 (2000b) 155-164.
S. Lestavel-Delattre, F. Martin-Nizard, V. Clayey, P. Testard, G. Favre, G. Doualin, H. S. Houssaini, J. M. Bard, P. Duriez, C. Delbart, et al., Cancer Res, 52 (1992) 3629-3635.
M. Hammel, P. Laggner, R. Prassl, Chem Phys Lipids, 123 (2003) 193-207.
I. J. Edwards, I. M. Berquin, H. Sun, T. O'Flaherty J, L. W. Daniel, M. J. Thomas, L. L. Rudd, R. L. Wykle, Y. Q. Chen, Clin Cancer Res, 10 (2004) 8275-8283.
T. Hevonoja, M. O. Pentikainen, M. T. Hyvonen, P. T. Kovanen, M. Ala-Korpela, Biochim Biophys Acta, 1488 (2000) 189-210.
L. Wang, M. T. Walsh, D. M. Small, Proc Natl Acad Sci USA, 103 (2006) 6871-6876.
J. P. Segrest, M. K. Jones, H. De Loof, N. Dashti, J Lipid Res, 42 (2001) 1346-1367.
L. P. Aggerbeck, F. J. Kezdy, A. M. Scanu, J Biol Chem, 251 (1976) 3823-3830.
S. Jayaraman, D. L. Gantz, O. Gursky, Biochemistry, 46 (2007) 5790-5797.
B. Heurtault, P. Saulnier, B. Pech, J. E. Proust, J. P. Benoit, Biomaterials, 24 (2003) 4283-4300.
P.-D. Duh, W. Yen, G.-C. Yen, J Amer Oil Chem Soc, 76 (1999) 201-204.
K. Miyashita, E. Nara, T. Ota, Bioscience, biotechnology, and biochemistry, 57 (1993) 1638-1640.
M. A. Khan, F. Shahidi, Journal of Food Lipids, 7 (2000) 143-150.
P. Zimet, Y. D. Livney, Food Hydrocol, 23 (2009) 7-7.
M. Moller, H. Botti, C. Batthyany, H. Rubbo, R. Radi, A. Denicola, J Biol Chem, 280 (2005) 8850-8854.
G. J. de Ruiz, R. Mertxe de, A. del Cerro, L. E. de Fernandez, P. Amiano, M. Dorronsoro, Lipids, 37 (2002) 333-341.
C. Calzada, R. Colas, N. Guillot, M. Guichardant, M. Laville, E. Vericel, M. Lagarde, Atherosclerosis, 208 (2010) 467-472.
B. Schuster, R. Prassl, F. Nigon, M. J. Chapman, P. Laggner, Proc Natl Acad Sci USA, 92 (1995) 2509-2513.
D. Shangguan, L. Meng, Z. C. Cao, Z. Xiao, X. Fang, Y. Li, D. Cardona, R. P. Witek, C. Liu, W. Tan, Anal Chem, 80 (2008) 721-728.
P. Q. Patek, J. L. Collins, M. Cohn, Nature, 276 (1978) 510-511.
O. O. Ogunwobi, C. Liu, Clin Exp Metastasis, 28 (2011) 721-731.
T. Nakagawa, Y. Ueyama, S. Nozaki, S. Yamashita, M. Menju, T. Funahashi, K. Kameda-Takemura, M. Kubo, K. Tokunaga, T. Tanaka, et al., J Clin Endocrinol Metab, 80 (1995) 92-96.
C. Peterson, S. Vitols, M. Rudling, H. Blomgren, F. Edsmyr, L. Skoog, Med Oncol Tumor Pharmacother, 2 (1985) 143-147.
L. Brissette, L. Falstrault, Biochimica et Biophysica Acta (BBA)—Lipids and Lipid Metabolism, 1165 (1992) 84-92.
Z. J. Ye, G. W. Go, R. Singh, W. Liu, A. R. Keramati, A. Mani, J Biol Chem, 287 (2012) 1335-1344.
N. Dippenaar, J. Booyens, D. Fabbri, P. Engelbrecht, I. E. Katzeff, S Afr Med J, 62 (1982a) 683-685.
W. P. Leary, K. M. Robinson, J. Booyens, N. Dippenaar, S Afr Med J, 62 (1982) 681-683.
N. Dippenaar, J. Booyens, D. Fabbri, I. E. Katzeff, S Afr Med J, 62 (1982b) 505-509.
S. V. Pande, J. F. Mead, Journal of Biological Chemistry, 243 (1968) 6180-6185.
W. Shaw, Clin Chem, 31 (1985) 1109-1115.
R. A. Siddiqui, K. Harvey, W. Stillwell, Chem Phys Lipids, 153 (2008) 47-56.
H. Ohkawa, N. Ohishi, K. Yagi, Anal Biochem, 95 (1979) 351-358.
X. Chen, Z. Zhong, Z. Xu, L. Chen, Y. Wang, Free Radic Res, 44 (2010) 587-604.
N. Lopez-Sanchez, J. R. Rodriguez, J. M. Frade, Mol Cancer Res, 5 (2007) 47-60.
A. M. Gardner, F. H. Xu, C. Fady, F. J. Jacoby, D. C. Duffey, Y. Tu, A. Lichtenstein, Free Radic Biol Med, 22 (1997) 73-83.
J. Chandra, A. Samali, S. Orrenius, Free Radic Biol Med, 29 (2000) 323-333.
N. Vanlangenakker, T. Vanden Berghe, D. V. Krysko, N. Festjens, P. Vandenabeele, Curr Mol Med, 8 (2008) 207-220.
W. J. de Villiers, Z. Song, M. S. Nasser, I. V. Deaciuc, C. J. McClain, J Gastroenterol Hepatol, 22 (2007) 414-422.
J. J. Chen, H. Bertrand, B. P. Yu, Free Radic Biol Med, 19 (1995) 583-590.
J. L. Toit-Kohn, L. Louw, A. M. Engelbrecht, J Nutr Biochem, 20 (2009) 106-114.
T. P. Szatrowski, C. F. Nathan, Cancer Res, 51 (1991) 794-798.
B. W. Shen, A. M. Scanu, F. J. Kezdy, Proc Natl Acad Sci USA, 74 (1977) 837-841.
D. Quilliot, E. Walters, P. Bohme, B. Lacroix, J. P. Bonte, J. C. Fruchart, P. Drouin, P. Duriez, O. Ziegler, Eur J Clin Nutr, 57 (2003) 496-503.
Bloomfield, Ann. Rev. Biophys. Bioeng., 10: 421-450 (1981).
Deamer and Bangham, Biochim. Biophys. Acta 443: 629-634 (1976),
Fraley et al., Proc. Natl. Acad. Sci. USA 76: 3348-3352 (1979).
Hope et al., Biochim. Biophys. Acta 812: 55-65 (1985).
Liposomes, ch. 1 (Ostro, ed., 1983); and Hope et al., Chem. Phys. Lip. 40: 89 (1986).
Malyer et al., Biochim. Biophys. Acta 858: 161-168 (1986).
Szoka et al., Ann. Rev. Biophys. Bioeng. 9:467 (1980).
Szoka and Papahadjopoulos, Proc. Natl. Acad. Sci. USA 75: 4194-4198 (1978).
Williams et al., Proc. Natl. Acad. Sci. USA 85: 242-246 (1988).

What is claimed is:

1. A composition comprising a lipid nanoparticle comprising a ω-3 polyunsaturated fatty acid and lacking another anti-cancer agent, wherein said lipid nanoparticle is about 15 nm to 30 nm in diameter, wherein said lipid nanoparticle exhibits unaltered polyunsaturated fatty acid, unaltered z-average particle size, unaltered peroxidation, unlatered polydispersity index, unaltered % transmittance and unaltered zeta potential over one month under ambient conditions.

2. A composition comprising a lipid nanoparticle consisting essentially of low density lipoprotein (LDL) and a ω-3 polyunsaturated fatty acid, wherein said lipid nanoparticle is about 15 nm to 30 nm in diameter, wherein said lipid nanoparticle exhibits unaltered polyunsaturated fatty acid, unaltered z-average particle size, unaltered peroxidation, unlatered polydispersity index, unaltered % transmittance and unaltered zeta potential over one month under ambient conditions.

3. A composition comprising a lipid nanoparticle and a therapeutically effective amount of a ω-3 polyunsaturated fatty acid not conjugated to another anti-cancer agent, wherein said lipid nanoparticle is about 15 nm to 30 nm in diameter, wherein said lipid nanoparticle exhibits unaltered polyunsaturated fatty acid, unaltered z-average particle size, unaltered peroxidation, unlatered polydispersity index, unaltered % transmittance and unaltered zeta potential over one month under ambient conditions.

4. The composition of claim 1, wherein the nanoparticle is a LDL or sLDL nanoparticle.

5. The composition of claim 1, wherein the ω-3 polyunsaturated fatty acid is docosahexaenoic acid (DHA).

6. The composition of claim 1, wherein the nanoparticle is a LDL or sLDL nanoparticle and further wherein the ω-3 polyunsaturated fatty acid is docosahexaenoic acid (DHA).

7. The composition of claim 4, wherein the LDL is human LDL.

8. The composition of claim 5, wherein DHA is incorporated into an LDL or sLDL nanoparticle.

9. The composition of claim 4, wherein ApoB100 is embedded in a phospholipid monolayer.

10. The composition of claim 1, wherein the composition is comprised in a pharmaceutically acceptable carrier.

11. A method for treating a subject having a cancer comprising administering an effective amount of a composition of claim 1 to the subject.

12. The method of claim 11, wherein the cancer is a breast cancer, lung cancer, head and neck cancer, prostate cancer, esophageal cancer, tracheal cancer, brain cancer, liver cancer, bladder cancer, stomach cancer, pancreatic cancer, adrenal cancer, ovarian cancer, uterine cancer, cervical cancer, testicular cancer, colon cancer, rectal cancer, blood cancer, or skin cancer.

13. The method of claim 12, wherein the composition is administered systemically.

14. The method of claim 12, wherein the composition is administered intravenously, intradermally, intratumorally, intramuscularly, intraperitoneally, or subcutaneously, or by infusion local or regional to a tumor site.

15. The method of claim 12, further comprising administering at least a second anticancer therapy to the subject.

16. The method of claim 15, wherein the second anticancer therapy is a surgical therapy, chemotherapy, radiation therapy, cryotherapy, hormonal therapy, toxin therapy, immunotherapy or cytokine therapy.

17. The method of claim 12, wherein the subject is a human, or a non-human mammal.

18. The method of claim 12, wherein said cancer is metastatic, recurrent or multi-drug resistant.

19. The method of claim 11, wherein said composition is administered at least a second time.

* * * * *

UNITED STATES PATENT AND TRADEMARK OFFICE
CERTIFICATE OF CORRECTION

PATENT NO. : 9,889,092 B2
APPLICATION NO. : 14/774637
DATED : February 13, 2018
INVENTOR(S) : Ian R. Corbin Page 1 of 1

It is certified that error appears in the above-identified patent and that said Letters Patent is hereby corrected as shown below:

In Claim 1, Column 35, Line 1, delete "unlatered" and insert --unaltered-- therefor.

In Claim 2, Column 35, Line 10, delete "unlatered" and insert --unaltered-- therefor.

In Claim 3, Column 35, Line 20, delete "unlatered" and insert --unaltered-- therefor.

Signed and Sealed this
Twenty-second Day of May, 2018

Andrei Iancu
*Director of the United States Patent and Trademark Office*